US009274110B2

(12) United States Patent
Tuaillon et al.

(10) Patent No.: US 9,274,110 B2
(45) Date of Patent: Mar. 1, 2016

(54) DIAGNOSIS METHOD OF ACTIVE TUBERCULOSIS

(75) Inventors: Edouard Tuaillon, Castelnau-le-Lez (FR); Pierre-Alain Rubbo, Montpellier (FR); Stephane Canaan, Marseilles (FR); Laurent Kremer, Montpellier (FR); Nicolas Nagot, Prades le Lez (FR); Philippe Van De Perre, Saint Vincent de Barbeyrargues (FR); Jean-Pierre Vendrell, Castelnau-le-Lez (FR)

(73) Assignees: Universite Montpellier 2 Sciences et Technique, Montpellier Cedex (FR); Universite Montpellier 1, Montpellier (FR); Centre Hospitalier Universitaire de Montpellier, Montpellier (FR); Centre National de La Recherche Scientifique, Paris (FR)

( * ) Notice: Subject to any disclaimer, the term of this patent is extended or adjusted under 35 U.S.C. 154(b) by 59 days.

(21) Appl. No.: 14/123,699

(22) PCT Filed: Jun. 1, 2012

(86) PCT No.: PCT/EP2012/060437
§ 371 (c)(1),
(2), (4) Date: Mar. 7, 2014

(87) PCT Pub. No.: WO2012/164088
PCT Pub. Date: Dec. 6, 2012

(65) Prior Publication Data
US 2014/0220599 A1 Aug. 7, 2014

(30) Foreign Application Priority Data
Jun. 3, 2011 (EP) .................................... 11168643

(51) Int. Cl.
G01N 33/53 (2006.01)
C07K 1/00 (2006.01)
G01N 33/569 (2006.01)

(52) U.S. Cl.
CPC .................................. *G01N 33/5695* (2013.01)

(58) Field of Classification Search
CPC ................................................ G01N 33/5695
See application file for complete search history.

(56) References Cited

U.S. PATENT DOCUMENTS
2007/0184073 A1 8/2007 Andersen

FOREIGN PATENT DOCUMENTS
WO WO 02/074903 A2 9/2002
WO WO 2004/104193 A2 12/2004

OTHER PUBLICATIONS

International search report dated Oct. 9, 2012 in corresponding PCT Application No. PCT/EP202/060437 filed Jun. 1, 2012.
Brockerhoff, H., and Jensen, R. G. (1974) Lipolytic Enzymes, Academic Press, New York.
Borgström, B., and Erlanson, C. (1984) Lipases, Elsevier, Amsterdam.
Panaitov, I., and Verger, R. (2000) Enzymatic reactions at interfaces: Interfacial and temporal organization of enzymatic lipolysis, In Physical Chemistry of Biological Interfaces (Baszkin, A., and Norde, W., Eds.), pp. 359-400, Marcel Dekker, Inc, New York, Basel.
Weldingh: "Assessing the Serodiagnostic Potential of 35 *Mycobacterium tuberculosis* Proteins and identification of Four Novel Serological Antigens", vol. 43, No. 1, Jan. 1, 2005; pp. 57-65.
Zhang G. et al.: "Screening and Assessing 11 *Mycobacterium tuberculosis* Proteins as Potential Serodiagnostical Markers for Discriminating TB Pateients from BCG Vaccinees", Genomincs Proteomics and Bioinformatics, Beijing Genomics Institute, Beijing, CN, vol. 7, No. 3, Sep. 1, 2009, pp. 107-115, XP026791702, ISSN:1672-0229.
M. Schue et al.: "Two cutinase-like proteins secreted by *Mycobacterium tuberculerosis* show very different lipolytic activities reflecting their physiological function", The FASEB Journal, vol. 24, No. 6, Jan. 26, 2010, pp. 1893-1903, XP055006732, ISSN:0892-6638.
Xu Guangxian et al.: "Hemolytic phospholipase Rv0183 of *Mycobacterium tuberculerosis* induces inflammatory response and apoptosis in alveolar macrophage RAW264.7 cells", Canadian Journal of Microbiology, NRC Research Press, CA, vol. 56, No. 11, Nov. 1, 2010, pp. 916-924, XP008142739, ISSN:0008-4166.
Karen Cotes et al.: "Characterization of an exported monoglyceride lipase from *Mycobacterium tuberculerosis* possibly involved in the metabolism of host cell membrane lipids", Biochemical Journal, vol. 408, No. 3, Dec. 15, 2007, p. 417, XP055006729, ISSN: 0264-6021.
K.C. Mishra et al.: "Functional Role of the PE Domain and Immunogenicity of the *Mycobacterium tuberculerosis* Triacylglycerol Hydrolase LipY", Infection and Immunity, vol. 76, No. 1, Oct. 15, 2007, pp. 127-140, XP055014993, ISSN:0019-9567.
C. Deb: "A Novel Lipase Belonging to the Hormone-sensitive Lipase Family Induced under Starvation to Utilize Stored Triacylglycerol *Mycobacterium tuberculerosis*", Journal of Biological Chemistry, vol. 281, No. 7, Jan. 3, 2006, pp. 3866-3875, XP055014975, ISSN:0021-9258.
Cotes K. et al.: "Lipolytic enzymes in *Mycobacterium tuberculerosis*", Applied Microbiology and Biotecnology, Springer, Berlin, DE, vol. 78, No. 5, Feb. 29, 2008, pp. 741-749, XP019586372, ISSN:1432-0614.
Belinda Brust et al.: "*Mycobacterium tuberculerosis* Lipolytic Enzymes as Potential Biomarkers for the Diagnosis of Active Tuberculerosis", PLOS One, vol. 6, No. 9, Sep. 22, 2011, p. E25078, XP055014990.
Robert Verger et al.: "Action of Phospholipase A at Interfaces*" The Journal of Biological Chemistry, vol. 248, No. 11, Jun. 10, 1973, pp. 4023-4034.

(Continued)

*Primary Examiner* — Albert Navarro
(74) *Attorney, Agent, or Firm* — RatnerPrestia

(57) ABSTRACT

The present invention relates to a method for the in vitro diagnosis of active tuberculosis, comprising a step of contacting lymphocytes of a patient suspected to have active tuberculosis with at least one protein of mycobacteria, said protein being an enzyme having a lipolytic activity, and a step of detecting the presence of specific activated lymphocytes.

10 Claims, 3 Drawing Sheets

(56) References Cited

OTHER PUBLICATIONS

Zhang H.: "PPe Protein (Rv3425) from DNA segment RD11 of *Mycobacterium tuberculosis*: a potential B-cell antiagen used for serological diagnosis to distinguish vaccinated controls from tuberculosis patients", European Society of Clinical Microbiology and Infectious Diseases, Clinical Microbiology and infenction, vol. 13, No. 2, Feb. 2007, pp. 139-145.

Stephane Canaan et al., "Expression and characterization of the protein Rv1399c from *Mycobacterium tuberculosis*", Eur. J. Biochem 271, Feb. 2004, pp. 3953-3961.

Sabine Daugelat et al.: "The RD1 proteins of *Mycobacterium tuberculosis*: espression in *Mycobacterium smegmatis* and biochemical characterization", Elsevier, Microbes and Infections 5 (2003) pp. v1082-v1095.

Min Zhang et al.: "Expression and characterization of the carboxyl esterase Rv3487c from *Mycobacterium tuberculosis*", Elsevier, Protein Expression & Purification 42 (2005) pp. 59-66.

DIAGNOSIS METHOD OF ACTIVE TUBERCULOSIS

CROSS REFERENCE TO RELATED APPLICATIONS

This application is a 371 application of International Application No. PCT/EP2012/080437, filed Jun. 1, 2012, which claims priority to European Patent Application EP11168643.2 filed Jun. 3, 2011, all of which are incorporated by reference in its entirety herein.

DESCRIPTION

The inventions relates to a diagnosis method of active tuberculosis.

Human tuberculosis (TB) is a highly contagious bacterial infection that is passed from person to person through the air. It is usually spread through contact with an infected person who is actively coughing or talking. TB disease is caused when the bacteria multiply inside the body, causing tissue and organ damage. Without treatment, half of those with TB disease will die.

Most people know TB as a disease of the lungs. However, not all TB disease is in the lungs. Around 40% of TB disease occurs in another part of the body. This happens when the bacteria spread outside of the lungs. In these cases, extrapulmonary TB is more difficult to diagnose since the patient does not have normal signs and symptoms associated with pulmonary TB. TB disease can also occur in the lymph glands, brain, spine, bones, kidneys, or other organs.

There are two forms of TB infection: active TB, also known as TB disease, and latent TB infection (LTBI).

A person who is TB-infected may not necessarily develop the disease. Some are able to control the infection, but unable to completely remove it from their bodies. In these cases, the infection remains, lying in an inactive state within granulomas. This is often described as LTBI. People with LTBI do not usually show any signs of TB symptoms so it can go unnoticed. LTBI may develop into active disease someday, often when the person's immune system becomes weakened. In fact, healthy people who are infected with latent TB have about 10% risk of converting to active disease each year over their lifetime. Thus, active TB is generally considered as the reactivation of mycobacteria from a latent form. Since this latent infection can become active at any time, it is usually monitored but not necessarily treated. By contrast, active TB that is the critical form of the disease and easily spread to other individuals, must be rapidly treated with up to four antibiotics during several months. Therefore, distinction between active and latent TB remains essential for the therapeutic care of infected patients.

Vaccination

An effective TB vaccine would be a major advance in the control of TB, but to date no such vaccine exists. The BCG vaccine is used in some countries and while this is thought to offer some protection against TB infection in children it is considered to have limited benefits in adults (around 50% protection). Additionally, BCG-vacinated people and individuals infected with nontuberculous *mycobacteria* (*mycobacteria* other than *M. tuberculosis*) may produce a positive tuberculin skin test (TST) result, even if they are not infected. These are the two most common causes of false positive TST results and can lead to unnecessary treatment for LTBI.

So there is a need to provide a diagnosis method with an optimal sensitivity, and well differentiates patient having an effective active TB.

Diagnosing Active TB
1. Active TB can be difficult to diagnose, especially in children, those who have weakened immune systems or those developing extrapulmonary TB. Beside medical examinations, the following tests used to determine if a patient has active TB:
Tuberculin Skin Test (TST),
Chest Radiograph (X-ray),
Sputum Smear Microscopy (SSM),
Culture, and
PGR (GeneXpert®).
Tuberculin Skin Test (TST)

The TST has been in existence for over 100 years. A suspension containing TB proteins is injected into the derma in the lower part of the arm. The injection site is examined by a trained healthcare professional 2-3 days later. If the person has TB, the body recognizes the proteins that were injected and responds by forming a lump where the TB proteins were injected.

The accuracy of the TST varies and can be affected by a previous TB vaccination (BCG), infection with nontuberculous bacteria, a weakened immune system and by other illnesses or medical treatments, Chest X-rays and Tomodensitometry Chest X-rays are used to check for lung abnormalities in people who have signs and symptoms of TB disease in the lungs. Although chest X-rays may suggest that TB disease is present, a chest X-ray alone cannot definitely diagnose a TB infection in the lungs or anywhere else in the body.

Sputum Smear Microscopy (SSM)

This is a simple laboratory test that examines sputum for bacteria using a microscope. This test also identifies non-TB bacteria, so it cannot always distinguish between TB and other infections. It is commonly used to diagnose TB disease because it can quickly determine if a person is infected. However, it sometimes gives a negative result even in people with TB disease so a negative result cannot be relied upon.

Culture

Culture techniques can be used to grow live TB bacteria in a laboratory. This is the standard reference method for detecting active TB as long as a suitable sample containing the TB bacteria can be obtained. TB can be cultured from a variety of specimens. This test can also provide information on which antibiotics would be effective in treating the infection. A major drawback of this test is the length of time it takes to get the results back (2-12 weeks) and the need to repeat the experiment from similar specimens of the same patient in order to obtain a positive result (i.e. poor sensitivity).

The GeneXpert® System

The GeneXpert® System is a closed and automated diagnostic platform that allow molecular identification of *M. tuberculosis* as well as resistance to rifampicin. It provides results from unprocessed sputum samples with limited technical training required for operators. This test has several limitations such as limited shelf-life of the diagnostic cartridges, some operating temperature and humidity restrictions, requirement for electricity supply, the need for annual servicing and calibration of each machine, the cost of the machine and each TB test as well as the need to multiply tests for increasing sensitivity.

Other tests have been developed using blood samples in order to diagnose active TB. As illustration, the following documents can be cited:

The international application WO 2009/129521 discloses the use of specific epitopes of mycobacterial proteins in order to specifically identify patient afflicted by active TB. Three proteins have been identified as harboring efficient epitopes: PTRP, PE-PGRS51 and LipC.

Zhang et al., Clin Microbiol Infect 2007; 13: 139-145, disclose that the comparative immunoreactivity of Rv3425, ESAT-6 and CFP-10 clearly distinguished between healthy subjects and TB patients. Moreover, Zhang et al. disclose that negligible antibody response obtained in the BCG-vaccinated healthy control group suggests that Rv3425, ESAT-6 and CFP-10 can be used for diagnosis of *M. tuberculosis* infection, even in geographical areas in which BCG vaccination is used routinely.

However, none of the methods disclosed in the art allows the practitioner to determine rapidly after the reactivation of the bacteria, the active TB in a patient, with a low amount of false-positive results.

Therefore, the invention proposes to overcome the above inconvenient.

One aim of the invention is to provide a new efficient method to precociously detect reactivation of mycobacteria.

Another aim of the invention is to provide an efficient method to distinguish active TB from LTBI.

Still another aim of the invention is to provide kits to carry out the method according to the invention.

The invention relates to a method for the in vitro diagnosis of active TB, comprising

- a step of contacting lymphocytes of a patient suspected to have active TB with at least one mycobacterial protein, said protein being an enzyme having a lipolytic activity, and
- a step of defecting the presence of specific activated lymphocytes.

The invention also relates to a Method for the in vitro diagnosis of active tuberculosis, comprising:

- a step of contacting a sample of purified B lymphocytes of a patient suspected to have an active tuberculosis with at least one protein of mycobacteria, said protein being an enzyme having a lipolytic activity and being able to hydrolyse lipids having a carbohydrate chain comprising at least 12 carbons,
- said sample being devoid of serum or of any component liable to contain soluble antibodies,
- a step of incubation during a determined time to allow the purified B lymphocytes to secrete specific antibodies directed against said enzyme having a lipolytic activity, and
- a step of detecting the presence of an immune complex comprising said antibodies and said enzyme having a lipolytic activity.

The invention is based on the unexpected observation made by the Inventors that mycobacterial enzymes expressing a lipolytic activity are powerful candidates for the enablement of a specific method allowing to discriminate active tuberculosis from latent tuberculosis.

The diagnosis proposed by the invention can be carried out in human but also in animals.

Hereafter, tuberculosis will be uniformly written "tuberculosis" or "TB".

In the invention, the term "lipase" is used to designate enzyme having lipolytic activity and include, phospholipases A, B, C or D, and lipases including triglyceride lipases, diglyceride lipases, or monoglyceride lipases.

During infection, *Mycobacterium tuberculosis* accumulates intracellular lipid-loaded inclusion bodies whose lipids probably originate from the host cell membrane degradation. There is now strong evidence supporting that fatty acids also represent a source of carbon during dormancy. *Mycobacterium tuberculosis* stores fatty acids in the form of triacylglycerol (TAG) as it enters in the nonreplicating persistence stage (Latent stage). Moreover, granulomas have been found to contain foamy macrophages that are cells bearing large amounts of neutral lipids surrounded by phospholipids in their cytoplasm. These lipid bodies are induced by the internalisation of bacteria and therefor providing a caron source for the survival and the reactivation of the pathogen. Overall, these findings support the view that enzymes involved in lipid degradation may fulfil important physiological functions and may participate in the extraordinary capacity of survival and reactivation of *Mycobacterium tuberculosis* from the infected host. Degradation of host lipis by *Mycobacterium tuberculosis* is likely to be performed by lipolytic enzymes, such lipases and phospholipases, including the cutinase family enzymes.

Lipases are water-soluble proteins having lipolytic activity belonging to esterase group and catalyzing the hydrolysis of insoluble substrates in water like triacylglycerol and phospholipids ester bonds [Alberghina, et al. (1991) *Lipases; Structure, Mechanism and Genetic Engineering*, Vol. 16, VCH, Weinheim, Fed Rep. Ger.; Wooley P., and Petersen, S. B. (1994) *Lipases; their structure, biochemistry and applications*, Cambridge Univerity Press, Cambridge; Brockerhoff, H., and Jensen, R. G. (1974) *Lipolytic Enzymes*, Academic Press, New York; Borgström, B., and Erlanson, C. (1984) *Lipases*, Elsevier, Amsterdam]. In this context, the catalytic reaction of lipolysis involves various interfacial processes and depends strongly on the structure of the lipid substrates present in oil-in-water emulsions, membrane bilayers, monolayers, micelles, and vesicles [Aloulou, et al. (2006) *Biochim. Biophys. Acta-Molecular and Cell Biology of Lipids* 1761, 995-1013]. The catalytic process can be described as a reversible lipase adsorption/desorption step occurring at the oil/water interface, followed by the formation of an interfacial enzyme substrate complex and the release of lipolysis products [Verger, R., et al. (1973) *J. Biol. Chem.* 248, 4023-4034; Panaitov, I., and Verger, R. (2000) Enzymatic reactions at inerfaces: Interfacial and temporal organization of enzymatic lipolysis, in *Physical Chemistry of Biological Interfaces* (Baszkin, A, and Norde; W., Eds.), pp 359-400, Marcel Dekker. Inc, New York, Base].

Among the *M. tuberculosis identified lipases,* 24 have been classified in a family of enzymes called the "Lip family". However, this classification is only based on the presence of the consensus sequence GXSXG, which is characteristic of esterases and members of the $\alpha/\beta$ hydrolase fold family. This classification does not allow the distinction between lipolytic enzymes (lipase) and non lipolytic enzymes (esterase).

For instance, LipH [Canaan, S. et al. (2004) *Eur. J. Biochem.* 271, 3953-3961], LipF [Zhang, M. et al. (2005) *Protein Expr Purif* 42, 59-66] and LipC (see example 1) were cloned and characterized but no long-chain triglycerides (TG) hydrolysis was detected.

On the contrary, the Inventors have demonstrated that "real" lipases, i.e. proteins having a long-chain hydrolysis activity, are useful for specifically diagnosing active TB, without cross-reaction with Latent TB samples. This includes the real lipase belonging to the Lip family, and any other real lipases that do not belong to the Lip family [Côtes K. et al. (2007) *Biochem J.* 408(3), 417-427].

The Inventors have hypothesized that lipolytic activity is high during the reactivation of the bacteria, thus leading to the method according to the invention which allows to specifically identify the reactivation only, i.e. the active TB.

On the contrary, in healthy individuals, or patient/individuals having LTBI, the immune system has not been in presence of the lipases according to the invention. Consequently, these healthy individuals or patient/individuals having LTBI would never been detected with the method according to the invention.

Therefore, the above mentioned lipases are used to carry out a method of diagnosis, preferably in vitro.

The method according to the invention is based on the detection of activated lymphocytes. "Activated lymphocytes" are single lymphocytes that are not naïve, i.e. lymphocytes that have been previously stimulated by specific antigens. This activation is accompanied by morphologic changes known as lymphocyte transformation, and the ability to secrete active molecules such as antibodies, cytokines, growth or death factors. These mechanisms of lymphocytes activation are well known in the art.

In a first step of the method according to the invention, activated lymphocytes of an individual, or a patient, suspected to have an active TB, are purified and contacted with at least one lipase of mycobacteria, preferably from *Mycobacterium tuberculosis*, said lipase having, as mentioned above, a lipolytic activity, or a biochemically identified lipolytic activity.

As mentioned above, LipC, LipH and LipF, which have not such lipase activity, are excluded de facto from the method according to the invention. Moreover, proteins from *Mycobacterium*, in particular from *Mycobacterium tuberculosis*, having no lipolytic activity are also excluded.

In a second step of the method according to the invention, the lipase-specific lymphocytes are detected, by means described hereafter.

It is clear for one having ordinary skill that the "activated lymphocytes" according to the invention are specific of the protein having a lipolytic activity. In other word, lymphocytes that have been activated by another protein devoid of lipolytic activity, would never been detected by the method according to the invention.

Thus, following the contacting of the lymphocytes of said patient/individual suspected to have active TB, and the detection of the active lymphocytes, the pathologist is able to determine if said patient/individual has active TB.

For instance, if no active lymphocytes are detected, it is possible to conclude that said patient is not afflicted by active TB. On the contrary, if activated lymphocytes are detected, the conclusion is that said patient/individual has active TB.

In the last case, it may also be possible, by quantifying the amount of active lymphocytes, to determine approximately the period from which bacteria have been reactivated.

On the contrary to the immunological standard method used in the art, which are based on the detection of the presence of antibodies in serum of patient/individual suspected to be afflicted by active TB, the method according to the invention allows a most precocious detection.

This precocity is due to the fact that activated lymphocytes are the first to be present in blood, prior to produce detectable compounds, such as antibodies, that can be detected by immunological techniques. In addition, detection of those activated lymphocytes specific for lipases involved in the reactivation of bacteria clearly permit the characterization of the active state of the disease. By contrast, detection of antibodies, such as in ELISA, does not necessarily reflect the active disease occurring at the time of detection but only a past exposition without indication of time since secreted antibodies after immunization could have a long half-life. Detection of such a low-level serological response to TB is caused by a previous exposure to *M. tuberculosis* sometime in the past and is called "serological scar". Therefore, the short half-life of these enzymes-specific activated lymphocytes circulating in the blood only during active TB, by contrast to antibodies, combined to the preferential production of some of the lipases used in the invention allow the precocious diagnostic of active TB.

In one advantageous embodiment, the invention relates to the method for the in vitro diagnosis of active TB as defined above, wherein said lymphocytes are B lymphocytes or T lymphocytes.

In the method according to the invention, the lymphocytes, and the activated lymphocytes are preferably B lymphocytes, secreting antibodies, and effector memory T lymphocytes, in particular T CD4+ and CD8+.

Another advantageous embodiment of the invention relates to the method for the in vitro diagnosis of active TB previously defined, wherein said enzyme having a lipolytic are able to hydrolyse lipids having a carbohydrate chain comprising at least 12 carbons.

The lipase according to the invention are the refore able to hydrolyse lipids having a carbohydrate chain comprising at least 12 carbons, preferably at least 14 carbons, in particular at least 16 carbons. At most, the carbohydrate chain has about 30 carbons.

The lipids defined in the invention are chosen among fatty acyls, glycerolipids, glycerophospholipids, sphingolipids, . . . .

These carbohydrates chains contained in the lipids are well known in the art, and can be mono or polysaturated, or not.

In one another advantageous embodiment, the invention relates to the method for the in vitro diagnosis of active TB as defined above, wherein said enzyme having a lipolytic activity is chosen among the group consisting of a phospholipase, preferably Rv3452, Rv3802c, PlcA, PlcB, PlcC or PlcD.

a lipase, preferably the lipase Rv1984c, a triacylglycerol hydrolase, preferably LipY, and a monoacylglycerol hydrolase, Rv0183.

The most advantageous lipases according to the invention are:

the protein having a phospholipase activity Rv3452, represented by the amino acid sequence SEQ ID NO: 1, the protein having a lipase activity Rv1984c, represented by the amino acid sequence SEQ ID NO: 2, the triacylglycerol hydrolase LipY (Rv3097c), represented by the amino acid sequence SEQ ID NO: 3, the monoacylglycerol hydrolase Rv0183 represented by the amino acid sequence SEQ ID NO: 4, the protein having a phospholipase activity PlcA (also named Rv2351c), represented by the amino acid sequence SEQ ID NO: 5.

the protein having a phospholipase activity PlcB (also named Rv2350c), represented by the amino acid sequence SEQ ID NO: 6, the protein having a phospholipase activity PlcC (also named Rv2349c), represented by the amino acid sequence SEQ ID NO: 7, and the protein having a phospholipase activity PlcD, represented by the amino acid sequence SEQ ID NO: 9 or the amino acid sequence SEQ ID NO: 8.

The above sequences correspond to the protein of *Mycobacterium tuberculosis*. However, the invention also encompasses peptides from other species of *Mycobacterium* involved in tuberculosis, such as *Mycobacterium kansasii*, *Mycobacterium marinum*, *Mycobacterium ulcerans*, *Mycobacterium avium*, *Mycobacterium avium* subsp. *avium*, *Mycobacterium avium* subsp. *paratuberculosis*, *Mycobacterium parascrofulaceum*, *Mycobacterium intracellulare*, *Mycobacterium leprae* and *Mycobacterium bovis*.

In one other embodiment of the invention, fragments of the above peptides harbouring immunogenic epitopes can be used in the method described above and hereafter.

The invention also encompasses variants of the above proteins, having a sequence identity of at least 75%, preferably at least 80%, more preferably at least 90%.

One another advantageous embodiment of the invention relates to the method for the in vitro diagnosis of active TB previously defined, wherein said lymphocytes are B lymphocytes, in particular B lymphocytes chosen among circulating plasmablasts and plasmocytes, said B lymphocytes secreting antibodies specifically directed against said enzyme having a lipolytic activity.

In this advantageous embodiment of the method according to the invention, B lymphocytes are detected.

This advantageous embodiment corresponds to an ELISpot (B-ELISpot, or ELISPOT B) technique wherein B cells expressing antibodies specifically directed against the lipase are detected.

The details of the method are disclosed in the Examples.

Briefly, the method consists to contact the lipase according to the invention with purified B lymphocytes from the patient/individual suspected to have active TB.

The purification of B lymphocytes can be achieved by any techniques well known in the art, for instance, by using the protocol disclosed in Greaves and Brown [Greaves and Brown. 1974, *The Journal of Immunology*, vol. 112 no. 1 420-42], or any adaptations thereof. Another protocol is disclosed in the Example section.

Preferably, the invention relates to the method for the in vitro diagnosis of active TB as defined above, wherein the step of detecting the presence of in vivo activated lymphocytes consists of detecting the secretion of said antibodies specifically directed against said enzyme having a lipolytic activity.

Advantageously, the method according to the invention allows the detection of activated B lymphocytes, by measuring their ability to secrete specific antibodies.

In order to limit interferences, or false positive, the B lymphocytes used in the method according to the invention are purified, and isolated from blood.

By "purified" it is meant in the invention that the B lymphocytes are isolated from the other cells contained in blood. The methods allowing the purification of B lymphocytes are well known in the art, and include immunological positive and/or negative selections (positive selection with specific marker expressed on B cells; negative selection by eliminating non B-Lymphocytes ceils . . . ).

A very important step during the isolation of the B lymphocytes is to eliminate any residual traces of serum, or fluid that is liable to contain antibodies. Repetitions of washing steps using ad hoc buffer, or separation on a sucrose gradient, or a combination of both, can be used.

The rosette method as described in Example 4 is particularly appropriated.

As mentioned above, the lymphocytes are obtained from blood of the patient/individual. In blood, it is possible to distinguish some B lymphocytes:
- the naïve B lymphocytes (that have never been activated by any antigen),
- the memory B lymphocytes (that have been activated by one antigen during an ancient infection),
- the transient B lymphocytes (incompletely differentiated naive cells), and
- the plasmablasts and the plasmocytes (that secrete antibodies), plasmablasts being detectable precociously during an infectious episode.

In vivo, if the patient/individual has a reactivation of the *mycobacteria*, lipase according to the invention will be expressed and accessible to the immune system. Then, B cells will be activated in order to produce specific antibodies directed against the lipase which have activated them.

The purified lymphocytes are then contacted with at least one lipase according to the invention for a determined period.

More advantageously, the invention relates to the method for the in vitro diagnosis of active TB as defined above, wherein said secretion is detected by measuring the formation of an immune complex between said antibodies and said enzyme having a lipolytic activity.

As mentioned above, the purified B lymphocytes are contacted with at least one lipase according to the invention. Thus, all the B lymphocytes able to produce antibodies will secrete these antibodies in the medium. Only antibodies that are specific to the lipase will form an immune complex (lipase/antibody immune complex), the other antibodies present being not able to form such immune complex.

A step of the method consists to remove the B lymphocytes, and the medium comprising them and the secreted antibodies. Then, only the lipase/antibody complex will be present. An specific immune complex is formed and can be defected.

Therefore, by common techniques allowing the detection of an immune complex, it would be possible to determine, and to quantify, the presence of such complex.

In the case of a bacterial reactivation, i.e. active TB, the method according to the invention would detect such immune complex. On the contrary, in the case of a healthy individual, or an individual having latent tuberculosis, no complex would be detected.

To summarize, the above method can be carry out as follows:
1. lipases according to the Invention are immobilized on a support.
2. purified B lymphocytes are contacted with said immobilized lipases to allow the formation of a binary lipase/anti lipase antibody complex.
3. after an appropriate incubation (from 1 h to 72 hours), lymphocytes are removed and the immobilized lipases are washed at least one time.
4. labelled antibodies directed against human Fc fragments are contacted with the immobilized lipases.
5. The ternary lipase/anti-lipase antibody/anti-Fc antibody complex is detected by appropriate means corresponding to the labelling molecule fixed on the anti-Fc antibody.

The step 3 mentioned above, the B lymphocytes are incubated with the immobilized enzyme having a lipolytic activity from about 1 hour to about 72 hours, preferably from about 24 hours to about 48 hours, in particular from about 16 hours to about 30 hours.

The above mentioned incubation times should no be too longer in order to limit the detection of memory B lymphocytes, which are present in a very low amount, but remain liable to secrete antibodies.

In still another advantageous embodiment the invention relates to the method for the in vitro diagnosis of active TB previously defined, wherein said lymphocytes are T lymphocytes, said lymphocytes secreting biomarkers such as cytokines, chemokines or growth factors after their activation.

In this advantageous embodiment of the method according to the invention, T lymphocytes are detected.

This advantageous embodiment corresponds to an ELISpot (T-ELISpot or ELISpot T) technique wherein T cells activated by the presentation of antigens corresponding to the lipases according to the invention are detected.

The details of the method are disclosed in the Examples.

Briefly, the method consists to contact the lipase according to the invention with purified peripheral blood mononuclear cells (PBMC) from the patient/individual suspected to have active TB.

The purification of PBMC can be achieved by any techniques well known in the art, for instance, by using gradient such as Ficoll® or Histopack® or any adaptations thereof. A protocol is disclosed in the Example section.

Advantageously, the invention relates to the method for the in vitro diagnosis of active TB above-described, wherein the step of detecting the presence of activated lymphocytes consists of detecting the secretion of at least one biomarker such as cytokine, chemokine or growth factor, said lymphocytes being activated by said enzyme having a lipolytic activity.

Following T cell development, matured, naïve T cells express the T ceil receptor (TCR)-CD3 complex. The TCR has an affinity for Major Histo Compatibility Complex (MHC) molecules.

Class II MHC proteins are generally found on the surface of specialised antigen-presenting cells (APCs), said Class II MHC molecules expressing parts of the peptides originating from exogenous bacteria or viruses. Class I MHC proteins are generally found on every nucleated cell of the body, said Class I MHC molecules expressing part of the peptides originating from degradation of cytosolic foreign proteins.

During an immune response, APCs cells express at their surface MHC molecules containing antigens of bacteria. Naïve T lymphocytes having a TCR complementary to the class MHC molecule-presenting antigen are then activated. This is the first step of the activation.

T cells having received the first signal have to be activated by a second signal implying surface co-stimulatory proteins involved in the MHC-TCR complex.

When the second signal is received, the T lymphocytes are then activated which allows itself to proliferate. Activated T ceils become effector or auxiliary lymphocytes secreting informative transmitters (cytokines, interferons, growth factors, chemokines . . . ).

When purifying PBMC, the antigen-experienced effector T lymphocytes are the predominant source of the early production of molecules (cytokines, interferon's, growth factors, chemokines, . . . ) following ex vivo antigen re-stimulation in the invention.

When purifying PBMC, the T lymphocytes having received the first signal are present, and can be stimulated in vitro by the antigen.

Thus, if the lipases according to the invention are contacted to the purified PBMC, only sensitized T lymphocytes that have been previously activated and differentiated Into effector cells can therefore produce the biomarkers corresponding to informative transmitters (cytokines, interferons, growth factors, chemokines . . . ).

Thus, if specific biomarkers are detected, that means that the PBMC stimulated in vitro by the lipases according to the invention contain active effector T lymphocytes, said T lymphocytes being activated and sensitized in vivo by APC cells expressing in their MHC molecules parts of said lipases. Measuring the presence of such specific effector T cells therefore diagnoses an ongoing infection, i.e. the bacteria have been reactivated.

On the contrary, if no specific biomarker is detected, that means that the PBMC do not contain lipase-specific effector T lymphocytes, i.e. no reactivation of the bacteria has occurred in vivo.

In a particularly advantageous embodiment, the invention relates to the method for the in vitro diagnosis of active TB defined above, wherein said secretion is detected by measuring the formation of an immune complex between at least one biomarker such as cytokine, chemokine or growth factor secreted by said activated T lymphocytes and antibodies specifically directed against said at least one biomarker such as cytokine, chemokine or growth factor.

Proteins such as IFN-γ, IP-10 (also known as CXCL10), IL-2, MCP-1 and IL-1RA are released in response to *Mycobacterium tuberculosis* antigen stimulation.

Therefore, the above biomarkers, and any other markers known in the art, can be detected with the method according to the invention as described above.

In one another advantageous embodiment, the invention relates to the method defined above, wherein said step of detecting the presence of activated lymphocytes is carried out by an immunological detection.

As mentioned above, activated T lymphocytes are able to produce/secrete biomarkers in the medium. Only antibodies that are specific to the said biomarkers will form an immune complex (biomarker/antibody complex), the other biomarkers present being not able to form such immune complex.

A step of the method consists to remove the T lymphocytes, and the medium comprising them and the secreted biomarkers. Then, only the biomarker/antibody complex will be present.

Therefore, by common techniques allowing the detection of an immune complex, it would be possible to determine, and to quantify, the presence of such complex.

In the case of active TB, the method according to the invention would defect such immune complex. On the contrary, in the case of a healthy individual, or an individual having LTBI, no complex would be detected.

To summarize, the above method can be carry out as follows:
1. Antibodies directed against specific biomarkers are immobilized on a support.
2. Purified PBMC are contacted with said immobilized antibodies directed against specific biomarkers to allow the formation of a binary biomarker/antibodies complex directed against specific biomarkers that will be secreted after lipase-speoific stimulation.
3. Lipase antigens according to the invention is added to PBMC.
4. After an appropriate incubation (from about 24 hours to about 6 days), PBMC are removed and the immobilized antibodies directed against specific biomarkers are washed at least one time.
5. Labelled antibodies directed against said biomarker are contacted with the immobilized antibodies directed against specific biomarkers.
6. The ternary complex antibodies directed against specific biomarkers-biomarker-labelled antibody anti-biomarker is detected by appropriate means corresponding to the labelling molecule fixed on the antibody anti-biomarker.

In both ELISpot disclosed above, the skilled person knows how to choose the appropriate labelling molecule to detect the ternary complex.

The invention also relates to a kit for the in vitro detection of active TB comprising
1. at least one protein of mycobacteria immobilised on a support, said protein being an enzyme having a lipolytic activity, and
2. antibodies, possibly labelled, directed against constant chain of immunoglobulins.

Advantageously, the invention relates to a kit for the in vitro detection of active tuberculosis comprising:
  at least one protein of mycobacteria immobilized on a support, said protein being an enzyme having a lipolytic activity, antibodies, possibly labelled, directed against constant chain of immunoglobulins, and
  means for specifically purifying B lymphocytes.

The kit may also further comprise positive and/or negative controls.

Support according to the kit described above and hereafter are for instance micro-titration plates, Elisa plates, plastic, Polyvinylidene Fluoride (PVDF) membrane . . . . The skilled person can easily determine the appropriate support.

For the detection procedure, antibodies used for the detection are usually labelled with a marker. Markers used for the labeling of the antibodies are chosen among markers commonly used by the skilled man in the art, and in particular are chosen among radio-isotopic marker, enzymes, fluorescent agents, luminescent agents, magnetic particles . . . .

The invention also relates to a kit for the in vitro detection of active TB comprising
  1. at least one protein of mycobacteria said protein being an enzyme having a lipolytic activity, and
  2. antibodies, immobilized on a support, directed against at least one biomarker secreted by activated T lymphocytes, Advantageously, the invention relates to a kit as defined above, wherein said enzyme having a lipolytic activity are able to hydrolyse lipids having a carbohydrate chain comprising at least 12 carbons.

More advantageously, the invention relates to a kit above defined, wherein said enzyme having a lipolytic activity is chosen among the group consisting of:
  a monoacylglycerol hydrolase, Rv0183,
  a phospholipase, preferably Rv3452, Rv3802c, PlcA, PlcB, PlcC or PlcD,
  a lipase, preferably Rv1984c, and
  a triacylglycerol hydrolase, preferably LipY.

Another advantageous embodiment of the invention related to a kit according as defined above, wherein said means specifically purifying B-lymphocytes are chosen among specific B cell specific antibodies, or density gradients, or a combination of the above.

The kit may also further comprise positive and/or negative controls, such as cells activated by polyclonal activator compounds or cultivated in cell culture media.

Advantageously, the invention relates to the kits above-defined, wherein said enzyme having a lipolytic activity are able to hydrolyse lipids having a carbohydrate chain comprising at least 12 carbons.

In particular, the invention relates to the kits previously defined, wherein said enzyme having a lipolytic activity is chosen among the group consisting of
  a phospholipase, preferably Rv3452, Rv3802c, PlcA, PlcB, PlcC or PlcD,
  a lipase, preferably Rv1984c,
  a triacylglycerol hydrolase, preferably LipY, and
  a monoacylglycerol hydrolase, Rv0183.

The invention will be better explained by the following examples and following FIGS. 1 to 3.

LEGEND TO THE FIGURES

FIGS. 1A and B represent the map of the pfasmid pSD24 obtained from pSD26.

Figure 2:
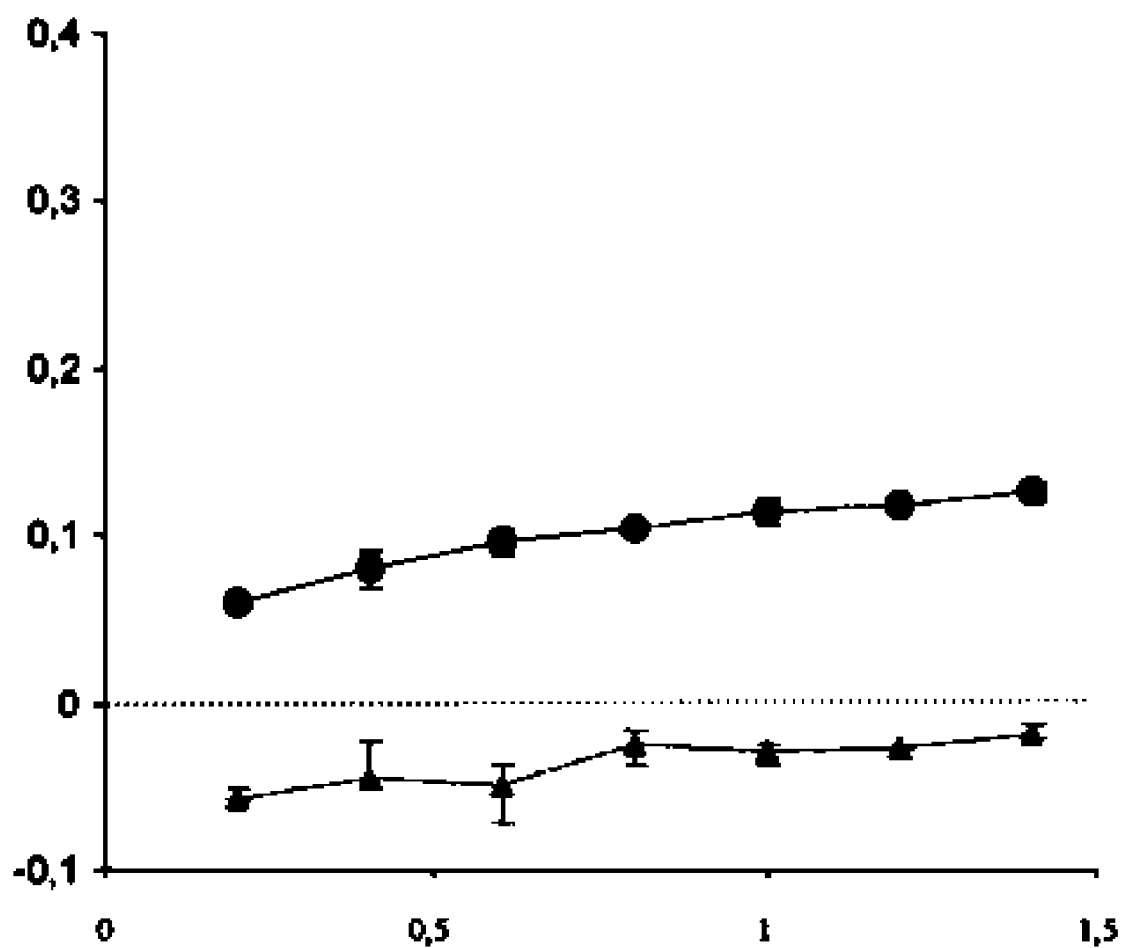
Figure 3:
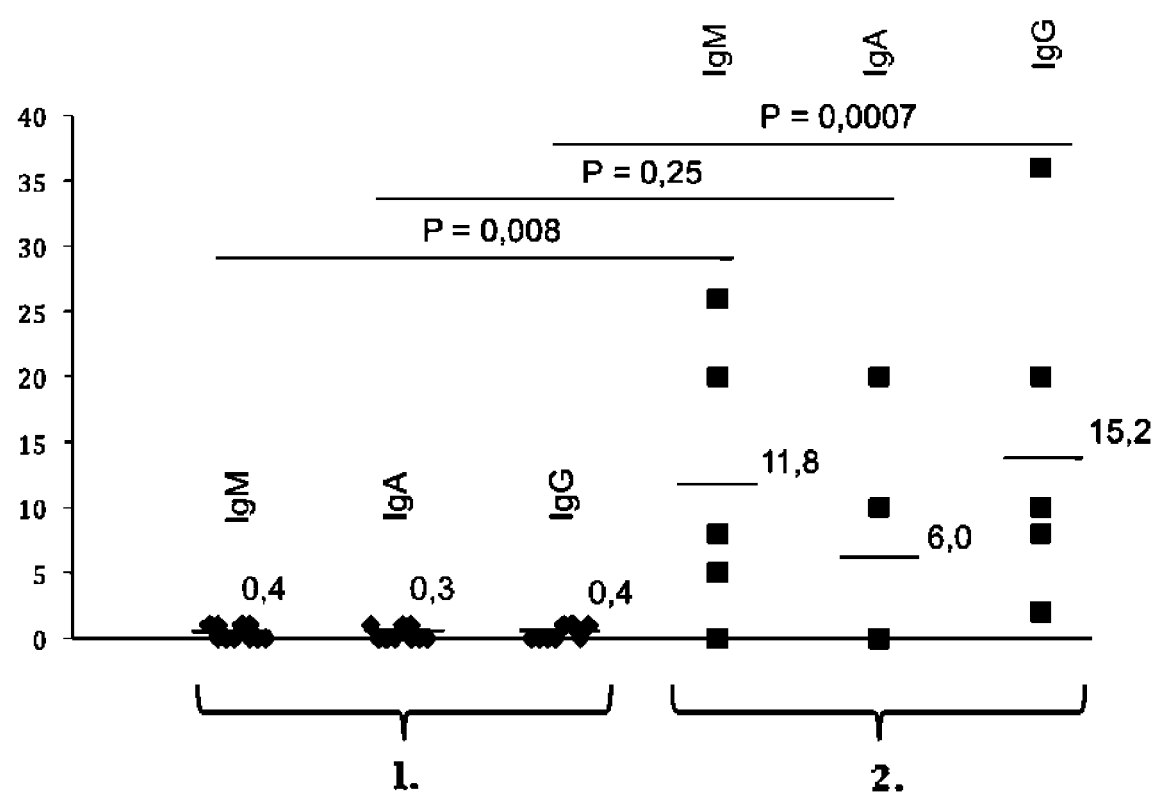

FIG. 2 represents a curve demonstrating the lipase activity of LipY. The graph represents the degradation of para-Nitrophenyl state with different amounts of protein. X-axis represents the amount of proteins (μg of cell wall); Y-axis represents the absorbance at 405 nm. Triangles: control mycobacteria. Circles: mycobacteria overexpression LipY FIG. 3 represents the results obtained with an ELISpot-B using LipY antigen.
  1. represents the patients with a latent tuberculosis (IGRA positive) and 2, the patients with active TB. Y-axis represents the antibodies secreting cells/$10^6$ B lymphocytes.

EXAMPLES

Example 1

LipC Is Not a Lipase per se, Whereas LipY is

Comparison of the lipase activity of Rv0220 (LIPC) and a cutinase from *F. solani* on paranitrophenyl ester family.

The activity of rLipC or cutinases was measured using p-nitrophenyl esters family (Sigma) with carbon chain lengths ranging from $C_2$ to $C_{14}$. Release of p-NP was monitored at 410 nm using a 96-well plates spectrophotomer and quantified using a calibration curve of pNP ($\epsilon_{(\lambda=410} $ nm)=30 mM$^{-1}$). Enzymatic reactions were performed in a 2.5 mM Tris buffer pH 8.0 containing 300 mM NaCl and 4 mM NaTDC at 357° C. over a period of 15 min in a final volume of 300 μL, containing various amount of enzyme and 1 mM substrate. Results are expressed as specific activity in international unit (U/mg) corresponding to 1 μmole of pNP released per minute and per mg of enzyme.

TABLE 1

| | Specific Activity (U · mg$^{-1}$) | |
| --- | --- | --- |
| Substrate | Rv0220 | Cutinase *F. solani* |
| p-Nitrophenyl esters | | |
| pNP-butyrate (C4) | 133 × 10$^{-3}$ | 382 ± 22 |
| pNP-valerate (C5) | 111 × 10$^{-3}$ | 78 ± 0.5 |
| pNP-caprylate (C8) | 22 × 10$^{-3}$ | 14 ± 3 |
| pNP-caprate (C10) | 2 × 10$^{-3}$ | 9 ± 1 |
| pNP-laurate (C12) | 0 | 1 ± 0.4 |
| pNP-myristate (C14) | 0 | 1 ± 0.2 |

The above table 1 demonstrates that LipC is not able to hydrolyse esters function associated with a fatty acyl chain having more than 10 carbons.

rLipC activity was also investigated using pH-stat, fluorescent and spectrophotometric assays for various lipids, as well as phospholipids, to detect lipase or phospholipase activity, respectively.

In contrast to cutinase or well known lipases, Rv0220 does not show any activity using pH-state, fluorescent and spectrophotometric assays using various lipids like triglycerides, diglycerides or monoglycerides as substrate, whatever the carbon chain length.

All these biochemical data clearly demonstrate that Rv0220 is not a lipolytic enzyme.

LipY

Lipolytic activity was assayed using cell wall preparations from *M. smegmatis* strains carrying the various lipase-expressing derivatives following induction with acetamide. Cell wall fraction from *M. smegmatis* harboring empty pSD26 was used as an internal control, so that the activity observed can be attributed only to the overexpressed lipases, para-Nitrophenyl stearate (Sigma) was used as the substrate, as it is specifically hydrolyzed by lipases and not by carboxyl esterases, which can hydrolyze substrates with short-chain acyl groups only (Zhang, M. et al. 2005. *Protein Expr. Purif.* 42:59-66). Assays were performed in 96-well plates (in a 100-l reaction mixture) containing increasing cell wall concentrations and a final concentration of 0.5 mM p-nitrophenylstearate (by diluting a 20 mM stock solution in acetonitrile with 100 mM Tris-HCl, ph 8.0). The mixture was incubated at 35° C., and the release of p-nitrophenol was measured spectrophotometrically at 405 nm after 40 min of reaction. The lipase activity was expressed as the difference between absorbance at 40 min and that at 0 min. Reactions were done in triplicate.

Results for LipY are shown in FIG. 2.

Example 2

Production of *M. tuberulosis* antigens: Rv0183, Rv1984c, Rv3452 and Rv3097c (LipY)

Bacterial Strains

*Escherichia coli* Rosetta pLysS was used for the expression of recombinant Rv0183 and Rv1984c, whereas C41(DE3) was used to overproduce Rv3452 [Côtes et al. (2007) *Biochem J* 408, 417-427; Schué et al. (2010) *Faseb J* 24, 1893-1903.]. LipY was expressed from recombinant *M. smegmatis* mc$^2$155 as reported [Mishra, et al. (2008) *Infect Immun* 76, 127-140] and the purification is described below.

*M. tuberculosis* Lipolytic Enzymes Expression Constructs

Figures 1A, 1B:
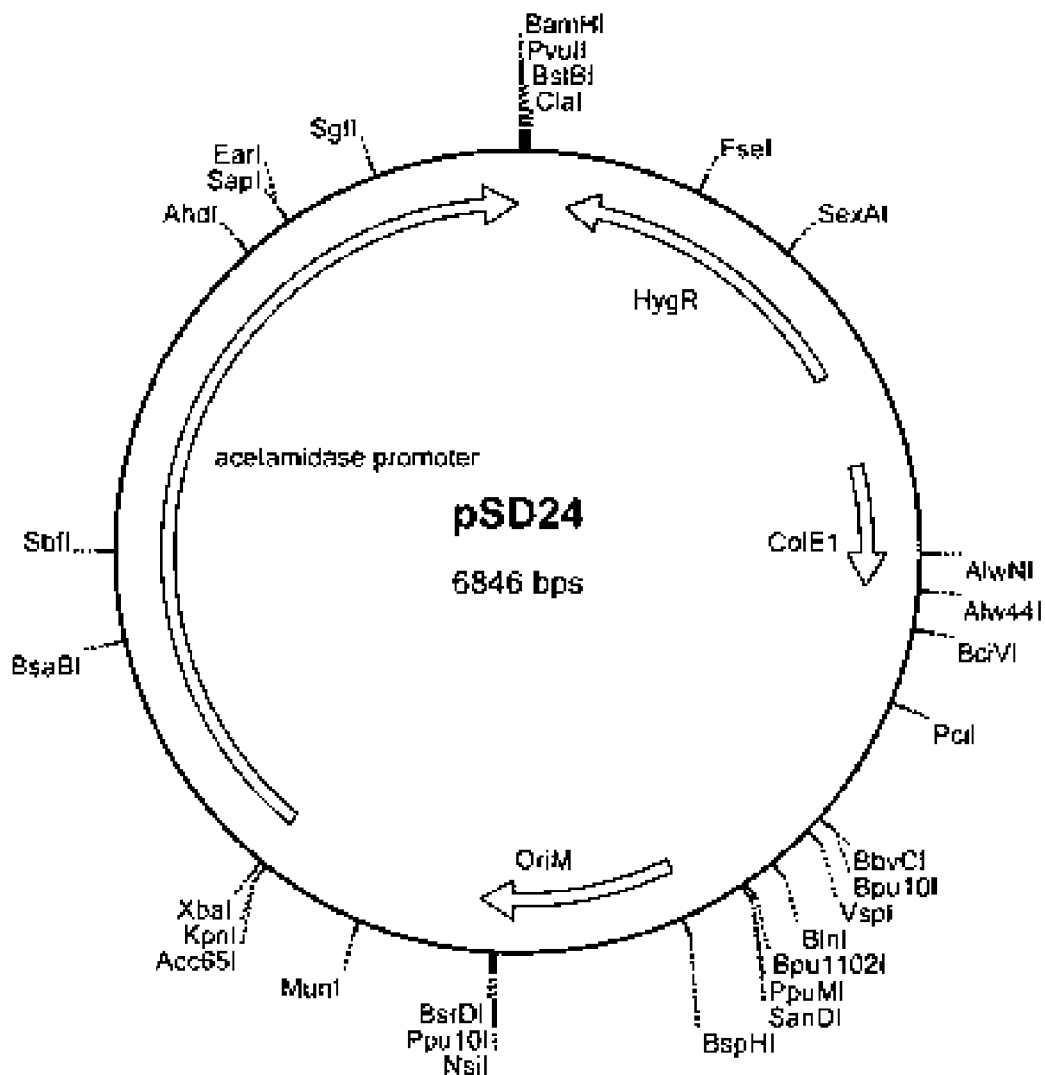
FIG. 1A represents the map of the plasmid pSD24 wherein restriction site are indicated.
FIG. 1B represents the multicloning site (MCS) of the pSD26 vector.

The Rv0183, Rv1984c, Rv3452 were amplified from cosmids MTCI28.23, MTCY39, MTCY13E12 and Rv3097c from BAC 48, respectively (obtained from the Pasteur Institute). Rv0183, Rv1984c and Rv3452 were cloned into pDest14 (Invitrogen) using the gateway technology, giving rise to pDest14-His-Rv0183, pDest14-His-RV 1984c and pDest14-His-Rv3452, respectively [Côtes et al. (2007) *Biochem J* 408, 417-427; Schué et al. (2010) *Faseb J* 24, 19893-1903]. The Rv3097c gene was coned into the acetamide-inducible pSD26 (FIG. 1) [Daugelat et al. (2003) *Microbes Infect* 5, 1082-1095] as described previously [Mishra, et al. (2008) *Infect Immun* 76, 127-140].

Expression and Purification of Rv0183, Rv1984c and Rv3452

*E. coli* strains carrying pDest14-His-Rv0183, pDest14-His-Rv 1984c or pDest14-His-Rv3452 were grown overnight in LB medium supplemented with appropriate antibiotics at 37° C. Cultures were then diluted 20 times with Terrific Broth and protein expression was induced with 1 mM isopropyl β-D-thiogalactoside (IPTG). Temperature was decreased to 25° C. and cultures were grown for another 16 hrs. Bacteria were then collected and resuspended in ice-cold lysis supplemented with DNAseI and MgSO$_4$. For purification of Rv0183, the supernatant obtained after cenirifugation was loaded onto a Ni$^{2+}$-Agarose column using a FPLC chromatography system (Amersham Biosciences). After washing with 10% of buffer B (consisting of Tris 10 mM pH 8.0, NaCl 150 mM with 500 mM imidazole), rRv0183 was eluted with 100% of buffer B. Eluted fractions containing the purified protein were pooled and further purified by size exclusion chromatograph (Superdex 200) in Tris 10 mM pH 8.0, NaCl 150 mM (buffer A).

Recombinant Rv1984c and Rv3452 were expressed only in an insoluble form and were refolded as already described [Schué et al. (2010) *Faseb J* 24, 1893-1903], Around 10-15 mg can be purified from 1 liter of culture. Enzymes were finally concentrated to 0.5-1 mg/ml and stored at −80° C. until further use.

Expression and Purification of Rv3097c

—Expression

Expression of recombinant Rv3097c was performed using *M. smegmatis* mc$^2$ 155 strain as previously reported [Mishra, et al. (2008) *Infect Immun* 76, 127-140] with some minor modifications. Briefly, a single transformed colony of *M. smegmatis* carrying the pSD26_LipY was used to inoculate 4 ml of 7H9 complete medium containing 50 μg/ml hygromycin B and used to inoculate 400 ml of culture medium for large-scale production. Cells were grown at 37° C. with shaking (220 rpm) until an OD$_{600nm}$ value of approximately 3 was reached. Expression of recombinant proteins was induced for by adding 0.2% acetamide for another 16 hrs.

—Purification

Bacteria were harvested and resuspended in ice-cold buffer consisting of 10 mM Tris/HCl buffer (pH 8.0) containing 150 mM NaCl and 1% N-lauroyl-sarcosine (sarcosyl) subsequently broken using a French press. The supernatant was recovered whereas the pellet was resuspended again and sonicated thrice during 30 seconds with 30 s breaks between each cycle and stirred overnight at 4° C. Both supernatants were then pooled and loaded onto a Ni$^{2+}$-NTA resin equilibrated with 10 mM Tris-HCl buffer (pH 8.0) containing 150 mM NaCl and 1% sarcosyl. The column was subsequently washed with buffer without detergent prior elution with increasing concentrations of imidazole. Fractions containing pure LipY were pooled and dialysed overnight against 10 mM Tris-HCl buffer (pH 8.0) containing 150 mM NaCl and further concentrated by ultrafiltration, generally leading to a final concentration of 0.5 mg/ml.

Example 3

Isolation and Purification of PBMC and B lymphocytes

Approximately, 20 ml of peripheral blood are collected in ethylenediamine tetraacetic acid (EDTA) tubes and peripheral blood mononuclear cells (PBMC) are cryoconserved before B cells are isolated and assayed.

PBMC are obtained from fresh blood samples by Histopaque® density centrifugation at 1,200 g for 20 min. PBMC are recovered from the ficoll-plasma interface and centrifuged three times in PBS-2% FCS before being resuspended in 1 ml complete culture medium. Once obtained, PBMC are mixed with an equal volume of FCS containing 20% DMSO at 4° C., stored for 24 h at −80° C. and then in liquid nitrogen. Upon removal from liquid nitrogen, cryovials were transferred to a 37° C. water bath for rapid thawing and then to a 50 ml centrifuge tube containing 5 ml of warm complete culture medium (RPMI 1640 supplemented with 10% FCS, 2 mM L-glutamine, 100 U/ml penicillin and 100 μg/ml streptomycin, all reagents from Eurobio, Les Ullis, France). Cells were centrifuged for 5 minutes at 1,200 g and resuspended in 1 ml of warm complete culture medium.

Meanwhile, 5 ml of fresh blood are centrifuged for 10 min at 50 g. Plasma and the layer of lymphocytes are removed before the red blood cell pellet is washed with PBS-2% FCS. The last pellet is resuspended in 1 ml of PBS-2% FCS.

Then, 30 ml of red blood cells previously purified and 10 ml of the Rosette Sep™ B cells enrichment cocktail are added in defrozen PBMC. The mixture is incubated for 20 min at room temperature with gentle shaking. Isolation of purified B lymphocytes is obtained by Histopaque® density centrifugation at 1,200 g for 20 min. Purified B cells are recovered from the ficoll-plasma interface and centrifuged three times in PBS-2% FCS before being resuspended in 1 ml complete culture medium. Finally, B cells are seeded into wells on ELISPOT plates.

Example 4

Enumeration of Spontaneous Plasmocytes and Plasmablastes Secreting *Mycobacterium tuberculosis*-Specific Antibodies (ELISPOT B)

The ability of B lymphocytes to spontaneously secrete specific antibodies directed against Rv0183, Rv1984c, Rv3452 and Rv3097c (LipY) is evaluated ex vivo using an ELISpot assay. Immobiion-P membrane 96-well plates (MAIPN 4550, Millipore, Molsheim, France) are activated with 50 µl of ethanol 70% for 10 min, washed three times with PBS and coated 18 h at 4° C. with about 3 µg/well of Rv0183, Rv1984c, R3452, Rv309c PlcA-D or Rv3802c in PBS. After three washes in PBS, each well is saturated with 100 µl of complete culture medium for 2 h at 37° C. All cells isolated after ficoll-hypaque separation were seeded at $2.5 \times 10^5$ cells/well in complete culture medium and incubated for about 24 hours at 37° C. in a 5% $CO_2$-humidifed atmosphere. After cell cultures are recovered, the plate is washed with PBS, PBS-0.05% Tween 20 and PBS again. Both biotinylated anti-IgM and phosphatase alkaline anti-IgG or both biotinylated anti-IgA and phosphatase alkaline anti-IgG monoclonal antibodies are added at 1:1,000 dilution in PBS and the plate is incubated 18 h at 4° C. or 6 h at 37° C. After washing with PBS, a solution of alkaline phosphatase-labeled streptavidin diluted at 1:1,000 in PBS was added and incubated 45 min at 37° C., The plates were washed three times with PBS and developed with the alkaline phosphatase conjugate substrate kit BCIP/NBT (a mixture of 5-bromo-4-chloro-3-indolyl phosphate and nitroblue tetrazolium) according to manufacturer's instructions (Bio-Rad). Once purple spots appeared, the reaction is stopped with three washes in PBS. 100 ml of AEC substrate (3-amino-9Ethylcarbazole) of peroxydase is added to each well for 20 min at room temperature. Reaction is stopped with 3 washes of distilled water. Each purple spot corresponds to a single cell capable of secreting anti-Rv0183, Rv1984c, Rv3452 or Rv3097c IgG antibodies while red spots corresponds to a single cell capable of secreting anti-Rv0183, Rv1984c, Rv3452 or Rv3097c IgM or IgA antibodies. Spots were counted by video camera imaging and computer-assisted analysis (KS ELISPOT; Carl Zeiss, Jena, Germany). Results with LipY Are Shown in FIG. 3

Theses results demonstrate that the ELISPOT 6 using LipY allows to discriminate patients with active TB (2.; n=5) from subjects with a latent TB (1.; n=10), at least for IgM and IgG ($P<0.05$).

Similar results are obtained for the other lipases Rv3452, Rv1984c, Rv0183 Rv3452, Rv3802c, PlcA, PlcB, PlcC and PlcD.

Material and Method of Example 4
Day 1:
Membrane activation: ethanol 70% addition, 50 µl per well, 5-10 minutes
3 washes, PBS (machine)
Add, per well, 100 µl antigen (tuberculin or lipases) at the following concentrations:
Tuberculin=4 µg/well (Cm=1 mg/ml) in PBS
LipY=5 µg/well (Cm=660 µg/ml) in PBS
Rv3452=6 µg/well (Cm=450 µg/ml) in carbonate buffer 100 mM, pH 9.6
Rv0183=4 µg/well (Cm=430 µg/ml) in PBS
Rv1984c=5 µg/well (Cm=600 µg/ml) in PBS
IgG/IgA: 10 µl of each in 3.2 ml PBS (100 µl/well)
Cover with adhesive and incubate over-night at 4° C. (72 h maximum or 6 h at 37° C.
Day 2:
3 washes, PBS
Membrane saturation with 100 µl enriched RPMI (de-complemented 10% FCS, glutamine and penicillin/streptomycin) for 2 h at 37° C.
Meanwhile, rosetteSep isolation of B lymphocytes from blood: In a 50 ml
Falcon tube, pour whole blood (maximum 15 ml).
Add equivalent volume of Rosettesep (GE Healthcare, for B cells: 50 µl per ml of whole blood).
Mix by reversing
Incubate for 20 minutes minimum.
B cell separation
Add volume 1/1 of PBS+2% FCS and mix by aspiration/overflow
On a same volume of Ficoll (same as whole blood) add carefully blood/PBS mix by using a 10 mL pipette
Centrifuge 21 min, 1200 g
Note the ring corresponding to B cells
Remove and discard carefully supernatant with a pipette
With a 5 ml pipette, remove by rotation the B cells ring and place in a 50 ml Falcon tube
Add 30 ml PBS, 2% FCS
Centrifuge: 6 min, 1200 g
Remove and carefully discard supernatant and wash the pellet with 30 ml PBS. 2% FCS
Wash 2 times.
Resuspend in 1 ml enriched RPMI
Count the cells
10 µl cells+10 µl acetic acid (erythrocytes lysis), mix, place on a counting device and count using a microscope.
Place 5000 B cells for control+in enriched RPMI and about 100,000 elsewhere
Cover plate with adhesive and incubate for 18 h-24 h at 37° C., $CO_2$ 5%
Be careful not to move the cells during this incubation in order to avoid smears.
Day 3:
Wash: 3×PBS, 3×PBS/Tween and 3×PBS (plate washer)
Revelation by adding 100 µl per well of mix PBS+antibodies 1/1000
Anti-IgG AP (alkaline phosphatase) conjugated
Anti-IgA hiotin-conjugated
Cover with adhesive and over-night at 4° C. or 6 h at 37° C.
Day 4
3 washes in PBS
For biotin-conjugated antibodies, add streptavidin-peroxidase, 1/1000 in PBS and incubate 45 min at 37° C.
Wash 3 times in PBS
Add AP substrate: NTB-BCIP (Biorad): 10 µl+10 µl B per ml of PBS (100 µl/well) during 20 min at room temperature (wash when spots appear)
Stop by 3 washes in PBS
Add peroxydase substrata AEC (100 µl/well) during 20 min at room temperature (4 ml distilled $H_2O$+2 drops of acetate buffer+1 drop of AEC chromogen+1 drop of 3% hydrogen peroxide)
Stop reaction by 3 washes in distillated water
Dry membrane at 37° C.
Punch membrane and glue spots on a transparent plastic adhesive
Read results (i.e. count spots).

Media
Enriched RPMI
Add to 500 ml bottles of RPMI 1640 medium
10% of decomplemented Foetal Calf Serum or FCS (56° C., 30 min)
1 ml of Streptomycin/Penicillin
5 ml of L-Glutamine
Enriched PBS
Add to 500 ml bottles of Phosphate Buffer Saline or PBS:
2% of FCS
1 ml of Streptomycin/Penicillin Example 5

Enumeration of Spontaneous *Mycobacterium tuberculosis*-Specific Interferon (IFN)-γ-Producing T lymphocytes (ELISpot T)

T cells stimulation by Rv0183, Rv1984c, Rv3452 or Rv3097c are measured by IFN-γ production using an IFN-γ-ELISpot kit (Diaclone, Besancon, France) according to manufacturer's instructions. PBMC are purified using ficoll-hipaque density gradient and $10^5$ PBMC are stimulated with individual *Mycobacterium tuberculosis*-specific antigens (2-8 µg/ml) or with 1 µg/ml phytohemagglutinin (PHA) for 24 h at 37° C. with 5% $CO_2$ on ELISpot plates (Millipore, Molsheim, France) that were pre-coated with anti-human IFN-γ capture antibodies, PBMC in culture medium without antigens were used as negative controls. At day 1, PBMC are removed, plate is incubated at 4° C. for 10 min with 100 ml of PBS-0.05% Tween 20 and 100 µl of detection antibody is added to each well after three more washes in 100 µl of PBS-0.05% Tween 20. Plate Is incubated at room temperature for 1 h 30 min and washed three more times with 100 µl of PBS-0.05% Tween 20. Then, 100 µl of streptavidin-alkaline phosphatase conjugate is added to every well and plate is incubated for 1 h at room temperature. The plates were washed three times with 100 µl of PBS-0.05% Tween 20 and developed with the alkaline phosphatase conjugate substrate kit BCIP/NBT according to manufacturer's instructions (Bio-Rad). Once purple spots appeared, the reaction is stopped with three washes in distilled water. Spots were counted by video camera imaging and computer-assisted analysis (KS ELISPOT: Carl Zeiss, Jena, Germany). The number of IFN-γ-secreting cells (ISC) is normalized per $10^6$ PBMC. The response to each antigen is considered as positive if the number of ISO was greater than twice the response vvithont antigen stimulation, after deduction of the background level.

Results are similar for LipY and the other lipases as those obtained with the method according to Example 4.

What is claimed is:

1. A method for the diagnosis of active tuberculosis, comprising:
   a step of contacting a sample of purified B lymphocytes of a patient suspected to have an active tuberculosis with at least one protein of mycobacteria, said protein being an enzyme having a lipolytic activity and being able to hydrolyse lipids having a carbohydrate chain comprising at least 12 carbons selected from the group consisting of:
   Rv3452 as set forth in SEQ ID NO: 1,
   Rv1984c as set forth in SEQ ID NO: 2,
   LipY, also called Rv3097c, as set forth in SEQ ID NO: 3,
   Rv0183 as set forth in SEQ ID NO: 4,
   PlcA, also called Rv2351c, as set forth in SEQ ID NO: 5,
   PlcB, also called Rv2350c, as set forth in SEQ ID NO: 6,
   PlcC, also called Rv2349c, as set forth in SEQ ID NO: 7, and
   PlcD, as set forth in SEQ ID NO: 9 or SEQ ID NO: 8,
   said sample being devoid of serum or of any fluid liable to contain soluble antibodies,
   a step of incubation during a determined time to allow the purified B lymphocytes to secrete specific antibodies directed against said enzyme having a lipolytic activity, and
   a step of detecting the presence of an immune complex comprising said antibodies and said enzyme having a lipolytic activity.

2. The method for the diagnosis of active tuberculosis according to claim 1, wherein B lymphocytes are chosen among plasmablasts and plasmocytes.

3. The method for the diagnosis of active tuberculosis according to claim 1, wherein the step of detecting the presence of activated B lymphocytes is carried out by an immunological detection.

4. The method for the diagnosis of active tuberculosis according to claim 1, wherein said determined time is from 1 hour to 72 hours.

5. A kit for the detection of active tuberculosis comprising:
   at least one protein of mycobacteria immobilised on a support, said protein being an enzyme having a lipolytic activity, selected from the group consisting of:
   Rv3452 as set forth in SEQ ID NO: 1,
   Rv1984c as set forth in SEQ ID NO: 2,
   LipY, also called Rv3097c, as set forth in SEQ ID NO: 3,
   Rv0183 as set forth in SEQ ID NO: 4,
   PlcA, also called Rv2351c, as set forth in SEQ ID NO: 5,
   PlcB, also called Rv2350c, as set forth in SEQ ID NO: 6,
   PlcC, also called Rv2349c, as set forth in SEQ ID NO: 7, and
   PlcD, as set forth in SEQ ID NO: 9 or SEQ ID NO: 8,
   antibodies directed against constant chain of immunoglobulins, and
   means for specifically purifying B lymphocytes.

6. The kit according to claim 5, wherein said means specifically purifying B-lymphocytes are chosen among specific B cell specific antibodies, or density gradients, or a combination of the above.

7. The method for the diagnosis of active tuberculosis according to claim 1, wherein said enzyme having a lipolytic activity is selected from the following enzymes:
Rv3452 as set forth in SEQ ID NO: 1,
Rv1984c as set forth in SEQ ID NO: 2, and
LipY as set forth in SEQ ID NO: 3.

8. The method for the diagnosis of active tuberculosis according to claim 1, wherein said determined time is from 6 hours to 48 hours.

9. The method for the diagnosis of active tuberculosis according to claim 1, wherein said determined time is from 16 h to 30 hours.

10. The kit according to claim 8, wherein the antibodies are labelled.

* * * * *

UNITED STATES PATENT AND TRADEMARK OFFICE
CERTIFICATE OF CORRECTION

PATENT NO. : 9,274,110 B2
APPLICATION NO. : 14/123699
DATED : March 1, 2016
INVENTOR(S) : Edouard Tuaillon et al.

Page 1 of 1

It is certified that error appears in the above-identified patent and that said Letters Patent is hereby corrected as shown below:

Claims

At Column 40, delete lines 19-20, claim 10, and insert

--10. The kit according to claim 5, wherein the antibodies are labeled.--

Signed and Sealed this
Third Day of May, 2016

Michelle K. Lee
*Director of the United States Patent and Trademark Office*

SEQUENCE LISTING

```
<160> NUMBER OF SEQ ID NOS: 10

<210> SEQ ID NO 1
<211> LENGTH: 194
<212> TYPE: PRT
<213> ORGANISM: Mycobacterium tuberculosis

<400> SEQUENCE: 1

Met His His His His His Glu Asn Leu Tyr Phe Gln Gly Cys Pro
1               5                   10                  15

Asp Ala Glu Val Val Phe Ala Arg Gly Thr Gly Glu Pro Pro Gly Leu
            20                  25                  30

Gly Arg Val Gly Gln Ala Phe Val Ser Ser Leu Arg Gln Gln Thr Asn
        35                  40                  45

Lys Ser Ile Gly Thr Tyr Gly Val Asn Tyr Pro Ala Asn Gly Asp Phe
    50                  55                  60

Leu Ala Ala Ala Asp Gly Ala Asn Asp Ala Ser Asp His Ile Gln Gln
65                  70                  75                  80

Met Ala Ser Ala Cys Arg Ala Thr Arg Leu Val Leu Gly Gly Tyr Ser
                85                  90                  95

Gln Gly Ala Ala Val Ile Asp Ile Val Thr Ala Ala Pro Leu Pro Gly
            100                 105                 110

Leu Gly Phe Thr Gln Pro Leu Pro Pro Ala Ala Asp Asp His Ile Ala
        115                 120                 125

Ala Ile Ala Leu Phe Gly Asn Pro Ser Gly Arg Ala Gly Gly Leu Met
    130                 135                 140

Ser Ala Leu Thr Pro Gln Phe Gly Ser Lys Thr Ile Asn Leu Cys Asn
145                 150                 155                 160

Asn Gly Asp Pro Ile Cys Ser Asp Gly Asn Arg Trp Arg Ala His Leu
                165                 170                 175

Gly Tyr Val Pro Gly Met Thr Asn Gln Ala Ala Arg Phe Val Ala Ser
            180                 185                 190

Arg Ile
```

```
<210> SEQ ID NO 2
<211> LENGTH: 199
<212> TYPE: PRT
<213> ORGANISM: Mycobacterium tuberculosis

<400> SEQUENCE: 2

Met His His His His His Glu Asn Leu Tyr Phe Gln Gly Asp Pro
1               5                   10                  15

Cys Ser Asp Ile Ala Val Val Phe Ala Arg Gly Thr His Gln Ala Ser
            20                  25                  30

Gly Leu Gly Asp Val Gly Glu Ala Phe Val Asp Ser Leu Thr Ser Gln
        35                  40                  45

Val Gly Gly Arg Ser Ile Gly Val Tyr Ala Val Asn Tyr Pro Ala Ser
    50                  55                  60

Asp Asp Tyr Arg Ala Ser Ala Ser Asn Gly Ser Asp Asp Ala Ser Ala
65                  70                  75                  80

His Ile Gln Arg Thr Val Ala Ser Cys Pro Asn Thr Arg Ile Val Leu
                85                  90                  95

Gly Gly Tyr Ser Gln Gly Ala Thr Val Ile Asp Leu Ser Thr Ser Ala
            100                 105                 110

Met Pro Pro Ala Val Ala Asp His Val Ala Ala Val Ala Leu Phe Gly
        115                 120                 125

Glu Pro Ser Ser Gly Phe Ser Ser Met Leu Trp Gly Gly Gly Ser Leu
    130                 135                 140

Pro Thr Ile Gly Pro Leu Tyr Ser Ser Lys Thr Ile Asn Leu Cys Ala
145                 150                 155                 160

Pro Asp Asp Pro Ile Cys Thr Gly Gly Gly Asn Ile Met Ala His Val
                165                 170                 175

Ser Tyr Val Gln Ser Gly Met Thr Ser Gln Ala Ala Thr Phe Ala Ala
            180                 185                 190

Asn Arg Leu Asp His Ala Gly
        195

<210> SEQ ID NO 3
<211> LENGTH: 455
<212> TYPE: PRT
<213> ORGANISM: Mycobacterium tuberculosis

<400> SEQUENCE: 3

Pro Glu Val Val Phe Ile His Gly Ser Val Val Ser Tyr Val Val Ala
1               5                   10                  15

Leu Pro Glu Val Met Ser Ala Ala Thr Asp Val Ala Ser Ile Gly
            20                  25                  30

Ser Val Val Ala Thr Ala Ser Gln Gly Val Ala Gly Ala Thr Thr Thr
        35                  40                  45

Val Leu Ala Ala Ala Glu Asp Glu Val Ser Ala Ala Ile Ala Ala Leu
    50                  55                  60

Phe Ser Gly His Gly Gln Asp Tyr Gln Ala Leu Ser Ala Gln Leu Ala
65                  70                  75                  80

Val Phe His Glu Arg Phe Val Gln Ala Leu Thr Gly Ala Ala Lys Gly
                85                  90                  95

Tyr Ala Ala Ala Glu Leu Ala Asn Ala Ser Leu Leu Gln Ser Glu Phe
            100                 105                 110

Ala Ser Gly Ile Gly Asn Gly Phe Ala Thr Ile His Gln Glu Ile Gln
        115                 120                 125
```

```
Arg Ala Pro Thr Ala Leu Ala Ala Gly Phe Thr Gln Val Pro Pro Phe
    130                 135                 140

Ala Ala Ala Gln Ala Gly Ile Phe Thr Gly Thr Pro Ser Gly Ala Ala
145                 150                 155                 160

Gly Phe Asp Ile Ala Ser Leu Trp Pro Val Lys Pro Leu Leu Ser Leu
                165                 170                 175

Ser Ala Leu Glu Thr His Phe Ala Ile Pro Asn Asn Pro Leu Leu Ala
            180                 185                 190

Leu Ile Ala Ser Asp Ile Pro Pro Leu Ser Trp Phe Leu Gly Asn Ser
        195                 200                 205

Pro Pro Pro Leu Leu Asn Ser Leu Leu Gly Gln Thr Val Gln Tyr Thr
    210                 215                 220

Thr Tyr Asp Gly Met Ser Val Val Gln Ile Thr Pro Ala His Pro Thr
225                 230                 235                 240

Gly Glu Tyr Val Val Ala Ile His Gly Gly Ala Phe Ile Leu Pro Pro
                245                 250                 255

Ser Ile Phe His Trp Leu Asn Tyr Ser Val Thr Ala Tyr Gln Thr Gly
            260                 265                 270

Ala Thr Val Gln Val Pro Ile Tyr Pro Leu Val Gln Glu Gly Gly Thr
        275                 280                 285

Ala Gly Thr Val Val Pro Ala Met Ala Gly Leu Ile Ser Thr Gln Ile
    290                 295                 300

Ala Gln His Gly Val Ser Asn Val Ser Val Val Gly Asp Ser Ala Gly
305                 310                 315                 320

Gly Asn Leu Ala Leu Ala Ala Gln Tyr Met Val Ser Gln Gly Asn
                325                 330                 335

Pro Val Pro Ser Ser Met Val Leu Leu Ser Pro Trp Leu Asp Val Gly
            340                 345                 350

Thr Trp Gln Ile Ser Gln Ala Trp Ala Gly Asn Leu Ala Val Asn Asp
        355                 360                 365

Pro Leu Val Ser Pro Leu Tyr Gly Ser Leu Asn Gly Leu Pro Pro Thr
    370                 375                 380

Tyr Val Tyr Ser Gly Ser Leu Asp Pro Leu Ala Gln Gln Ala Val Val
385                 390                 395                 400

Leu Glu His Thr Ala Val Val Gln Gly Ala Pro Phe Ser Phe Val Leu
                405                 410                 415

Ala Pro Trp Gln Ile His Asp Trp Ile Leu Leu Thr Pro Trp Gly Leu
            420                 425                 430

Leu Ser Trp Pro Gln Ile Asn Gln Gln Leu Gly Ile Ala Ala Ser Asp
        435                 440                 445

Ile His His His His His His
    450                 455

<210> SEQ ID NO 4
<211> LENGTH: 279
<212> TYPE: PRT
<213> ORGANISM: Mycobacterium tuberculosis

<400> SEQUENCE: 4

Gly Thr Thr Thr Arg Thr Glu Arg Asn Phe Ala Gly Ile Gly Asp Val
1               5                   10                  15

Arg Ile Val Tyr Asp Val Trp Thr Pro Asp Thr Ala Pro Gln Ala Val
                20                  25                  30

Val Val Leu Ala His Gly Leu Gly Glu His Ala Arg Arg Tyr Asp His
            35                  40                  45
```

Val Ala Gln Arg Leu Gly Ala Ala Gly Leu Val Thr Tyr Ala Leu Asp
    50                  55                  60

His Arg Gly His Gly Arg Ser Gly Gly Lys Arg Val Leu Val Arg Asp
65                  70                  75                  80

Ile Ser Glu Tyr Thr Ala Asp Phe Asp Thr Leu Val Gly Ile Ala Thr
                85                  90                  95

Arg Glu Tyr Pro Gly Cys Lys Arg Ile Val Leu Gly His Ser Met Gly
                100                 105                 110

Gly Gly Ile Val Phe Ala Tyr Gly Val Glu Arg Pro Asp Asn Tyr Asp
            115                 120                 125

Leu Met Val Leu Ser Ala Pro Ala Val Ala Gln Asp Leu Val Ser
    130                 135                 140

Pro Val Ala Val Ala Ala Lys Leu Leu Gly Val Val Pro Gly
145                 150                 155                 160

Leu Pro Val Gln Glu Leu Asp Phe Thr Ala Ile Ser Arg Asp Pro Glu
                165                 170                 175

Val Val Gln Ala Tyr Asn Thr Asp Pro Leu Val His Gly Arg Val
            180                 185                 190

Pro Ala Gly Ile Gly Arg Ala Leu Leu Gln Val Gly Glu Thr Met Pro
        195                 200                 205

Arg Arg Ala Pro Ala Leu Thr Ala Pro Leu Leu Val Leu His Gly Thr
210                 215                 220

Asp Asp Arg Leu Ile Pro Ile Glu Gly Ser Arg Arg Leu Val Glu Cys
225                 230                 235                 240

Val Gly Ser Ala Asp Val Gln Leu Lys Glu Tyr Pro Gly Leu Tyr His
                245                 250                 255

Glu Val Phe Asn Glu Pro Glu Arg Asn Gln Val Leu Asp Asp Val Val
            260                 265                 270

Ala Trp Leu Thr Glu Arg Leu
        275

<210> SEQ ID NO 5
<211> LENGTH: 512
<212> TYPE: PRT
<213> ORGANISM: Mycobacterium tuberculosis

<400> SEQUENCE: 5

Met Ser Arg Arg Glu Phe Leu Thr Lys Leu Thr Gly Ala Gly Ala Ala
1               5                   10                  15

Ala Phe Leu Met Asp Trp Ala Pro Val Ile Glu Lys Ala Tyr Gly
            20                  25                  30

Ala Gly Pro Cys Pro Gly His Leu Thr Asp Ile Glu His Ile Val Leu
        35                  40                  45

Leu Met Gln Glu Asn Arg Ser Phe Asp His Tyr Phe Gly Thr Leu Ser
    50                  55                  60

Ser Thr Asn Gly Phe Asn Ala Ala Ser Pro Ala Phe Gln Gln Met Gly
65                  70                  75                  80

Trp Asn Pro Met Thr Gln Ala Leu Asp Pro Ala Gly Val Thr Ile Pro
                85                  90                  95

Phe Arg Leu Asp Thr Thr Arg Gly Pro Phe Leu Asp Gly Glu Cys Val
                100                 105                 110

Asn Asp Pro Glu His Gln Trp Val Gly Met His Leu Ala Trp Asn Gly
            115                 120                 125

Gly Ala Asn Asp Asn Trp Leu Pro Ala Gln Ala Thr Arg Ala Gly
        130                 135                 140

-continued

```
Pro Tyr Val Pro Leu Thr Met Gly Tyr Tyr Thr Arg Gln Asp Ile Pro
145                 150                 155                 160

Ile His Tyr Leu Leu Ala Asp Thr Phe Thr Ile Cys Asp Gly Tyr His
                165                 170                 175

Cys Ser Leu Leu Thr Gly Thr Leu Pro Asn Arg Leu Tyr Trp Leu Ser
            180                 185                 190

Ala Asn Ile Asp Pro Ala Gly Thr Asp Gly Gly Pro Gln Leu Val Glu
        195                 200                 205

Pro Gly Phe Leu Pro Leu Gln Gln Phe Ser Trp Arg Ile Met Pro Glu
    210                 215                 220

Asn Leu Glu Asp Ala Gly Val Ser Trp Lys Val Tyr Gln Asn Lys Gly
225                 230                 235                 240

Leu Gly Arg Phe Ile Asn Thr Pro Ile Ser Asn Asn Gly Leu Val Gln
                245                 250                 255

Ala Phe Arg Gln Ala Ala Asp Pro Arg Ser Asn Leu Ala Arg Tyr Gly
            260                 265                 270

Ile Ala Pro Thr Tyr Pro Gly Asp Phe Ala Ala Asp Val Arg Ala Asn
        275                 280                 285

Arg Leu Pro Lys Val Ser Trp Leu Val Pro Asn Ile Leu Gln Ser Glu
    290                 295                 300

His Pro Ala Leu Pro Val Ala Leu Gly Ala Val Ser Met Val Thr Ala
305                 310                 315                 320

Leu Arg Ile Leu Leu Ser Asn Pro Ala Val Trp Glu Lys Thr Ala Leu
                325                 330                 335

Ile Val Ser Tyr Asp Glu Asn Gly Gly Phe Phe Asp His Val Thr Pro
            340                 345                 350

Pro Thr Ala Pro Pro Gly Thr Pro Gly Glu Phe Val Thr Val Pro Asn
        355                 360                 365

Ile Asp Ala Val Pro Gly Ser Gly Gly Ile Arg Gly Pro Leu Gly Leu
    370                 375                 380

Gly Phe Arg Val Pro Cys Ile Val Ile Ser Pro Tyr Ser Arg Gly Pro
385                 390                 395                 400

Leu Met Val Ser Asp Thr Phe Asp His Thr Ser Gln Leu Lys Leu Ile
                405                 410                 415

Arg Ala Arg Phe Gly Val Pro Val Pro Asn Met Thr Ala Trp Arg Asp
            420                 425                 430

Gly Val Val Gly Asp Met Thr Ser Ala Phe Asn Phe Ala Thr Pro Pro
        435                 440                 445

Asn Ser Thr Arg Pro Asn Leu Ser His Pro Leu Leu Gly Ala Leu Pro
    450                 455                 460

Lys Leu Pro Gln Cys Ile Pro Asn Val Val Leu Gly Thr Thr Asp Gly
465                 470                 475                 480

Ala Leu Pro Ser Ile Pro Tyr Arg Val Pro Tyr Pro Gln Val Met Pro
                485                 490                 495

Thr Gln Glu Thr Thr Pro Val Arg Gly Thr Pro Ser Gly Leu Cys Ser
            500                 505                 510
```

<210> SEQ ID NO 6
<211> LENGTH: 512
<212> TYPE: PRT
<213> ORGANISM: Mycobacterium tuberculosis

<400> SEQUENCE: 6

```
Met Thr Arg Arg Gln Phe Phe Ala Lys Ala Ala Ala Thr Thr Ala
1               5                   10                  15

Gly Ala Phe Met Ser Leu Ala Gly Pro Ile Ile Glu Lys Ala Tyr Gly
                20                  25                  30

Ala Gly Pro Cys Pro Gly His Leu Thr Asp Ile Glu His Ile Val Leu
            35                  40                  45

Leu Met Gln Glu Asn Arg Ser Phe Asp His Tyr Phe Gly Thr Leu Ser
        50                  55                  60

Asp Thr Arg Gly Phe Asp Asp Thr Thr Pro Val Val Phe Ala Gln
65                  70                  75                  80

Ser Gly Trp Asn Pro Met Thr Gln Ala Val Asp Pro Ala Gly Val Thr
                85                  90                  95

Leu Pro Tyr Arg Phe Asp Thr Thr Arg Gly Pro Leu Val Ala Gly Glu
            100                 105                 110

Cys Val Asn Asp Pro Asp His Ser Trp Ile Gly Met His Asn Ser Trp
        115                 120                 125

Asn Gly Gly Ala Asn Asp Asn Trp Leu Pro Ala Gln Val Pro Phe Ser
130                 135                 140

Pro Leu Gln Gly Asn Val Pro Val Thr Met Gly Phe Tyr Thr Arg Arg
145                 150                 155                 160

Asp Leu Pro Ile His Tyr Leu Leu Ala Asp Thr Phe Thr Val Cys Asp
                165                 170                 175

Gly Tyr Phe Cys Ser Leu Leu Gly Gly Thr Thr Pro Asn Arg Leu Tyr
            180                 185                 190

Trp Met Ser Ala Trp Ile Asp Pro Asp Gly Thr Asp Gly Gly Pro Val
        195                 200                 205

Leu Ile Glu Pro Asn Ile Gln Pro Leu Gln His Tyr Ser Trp Arg Ile
210                 215                 220

Met Pro Glu Asn Leu Glu Asp Ala Gly Val Ser Trp Lys Val Tyr Gln
225                 230                 235                 240

Asn Lys Leu Leu Gly Ala Leu Asn Asn Thr Val Val Gly Tyr Asn Gly
                245                 250                 255

Leu Val Asn Asp Phe Lys Gln Ala Ala Asp Pro Arg Ser Asn Leu Ala
            260                 265                 270

Arg Phe Gly Ile Ser Pro Thr Tyr Pro Leu Asp Phe Ala Ala Asp Val
        275                 280                 285

Arg Asn Asn Arg Leu Pro Lys Val Ser Trp Val Leu Pro Gly Phe Leu
290                 295                 300

Leu Ser Glu His Pro Ala Phe Pro Val Asn Val Gly Ala Val Ala Ile
305                 310                 315                 320

Val Asp Ala Leu Arg Ile Leu Leu Ser Asn Pro Ala Val Trp Glu Lys
                325                 330                 335

Thr Ala Leu Ile Val Asn Tyr Asp Glu Asn Gly Gly Phe Phe Asp His
            340                 345                 350

Val Val Pro Pro Thr Pro Pro Gly Thr Pro Gly Glu Phe Val Thr
        355                 360                 365

Val Pro Asp Ile Asp Ser Val Pro Gly Ser Gly Ile Arg Gly Pro
370                 375                 380

Ile Gly Leu Gly Phe Arg Val Pro Cys Leu Val Ile Ser Pro Tyr Ser
385                 390                 395                 400

Arg Gly Pro Leu Met Val His Asp Thr Phe Asp His Thr Ser Thr Leu
            405                 410                 415
```

-continued

```
Lys Leu Ile Arg Ala Arg Phe Gly Val Pro Val Pro Asn Leu Thr Ala
                420                 425                 430
Trp Arg Asp Ala Thr Val Gly Asp Met Thr Ser Thr Phe Asn Phe Ala
                435                 440                 445
Ala Pro Pro Asn Pro Ser Lys Pro Asn Leu Asp His Pro Arg Leu Asn
450                 455                 460
Ala Leu Pro Lys Leu Pro Gln Cys Val Pro Asn Ala Val Leu Gly Thr
465                 470                 475                 480
Val Thr Lys Thr Ala Ile Pro Tyr Arg Val Pro Phe Pro Gln Ser Met
                485                 490                 495
Pro Thr Gln Glu Thr Ala Pro Thr Arg Gly Ile Pro Ser Gly Leu Cys
                500                 505                 510

<210> SEQ ID NO 7
<211> LENGTH: 508
<212> TYPE: PRT
<213> ORGANISM: Mycobacterium tuberculosis

<400> SEQUENCE: 7

Met Ser Arg Arg Ala Phe Leu Ala Lys Ala Ala Gly Ala Gly Ala Ala
1               5                   10                  15
Ala Val Leu Thr Asp Trp Ala Ala Pro Val Ile Glu Lys Ala Tyr Gly
                20                  25                  30
Ala Gly Pro Cys Ser Gly His Leu Thr Asp Ile Glu His Ile Val Leu
            35                  40                  45
Cys Leu Gln Glu Asn Arg Ser Phe Asp His Tyr Phe Gly Thr Leu Ser
        50                  55                  60
Ala Val Asp Gly Phe Asp Thr Pro Thr Pro Leu Phe Gln Gln Lys Gly
65                  70                  75                  80
Trp Asn Pro Glu Thr Gln Ala Leu Asp Pro Thr Gly Ile Thr Leu Pro
                85                  90                  95
Tyr Arg Ile Asn Thr Thr Gly Gly Pro Asn Gly Val Gly Glu Cys Val
                100                 105                 110
Asn Asp Pro Asp His Gln Trp Ile Ala Ala His Leu Ser Trp Asn Gly
            115                 120                 125
Gly Ala Asn Asp Gly Trp Leu Pro Ala Gln Ala Arg Thr Arg Ser Val
        130                 135                 140
Ala Asn Thr Pro Val Val Met Gly Tyr Tyr Ala Arg Pro Asp Ile Pro
145                 150                 155                 160
Ile His Tyr Leu Leu Ala Asp Thr Phe Thr Ile Cys Asp Gln Tyr Phe
                165                 170                 175
Ser Ser Leu Leu Gly Gly Thr Met Pro Asn Arg Leu Tyr Trp Ile Ser
                180                 185                 190
Ala Thr Val Asn Pro Asp Gly Asp Gln Gly Pro Gln Ile Val Glu
            195                 200                 205
Pro Ala Ile Gln Pro Lys Leu Thr Phe Thr Trp Arg Ile Met Pro Gln
        210                 215                 220
Asn Leu Ser Asp Ala Gly Ile Ser Trp Lys Val Tyr Asn Ser Lys Leu
225                 230                 235                 240
Leu Gly Gly Leu Asn Asp Thr Ser Leu Ser Arg Asn Gly Tyr Val Gly
                245                 250                 255
Ser Phe Lys Gln Ala Ala Asp Pro Arg Ser Asp Leu Ala Arg Tyr Gly
                260                 265                 270
Ile Ala Pro Ala Tyr Pro Trp Asp Phe Ile Arg Asp Val Ile Asn Asn
            275                 280                 285
```

```
Thr Leu Pro Gln Val Ser Trp Val Val Pro Leu Thr Val Glu Ser Glu
            290                 295                 300

His Pro Ser Phe Pro Val Ala Val Gly Ala Val Thr Ile Val Asn Leu
305                 310                 315                 320

Ile Arg Val Leu Leu Arg Asn Pro Ala Val Trp Glu Lys Thr Ala Leu
                325                 330                 335

Ile Ile Ala Tyr Asp Glu His Gly Phe Phe Asp His Val Thr Pro
                340                 345                 350

Leu Thr Ala Pro Glu Gly Thr Pro Gly Glu Trp Ile Pro Asn Ser Val
                355                 360                 365

Asp Ile Asp Lys Val Asp Ser Gly Gly Ile Arg Gly Pro Ile Gly
370                 375                 380

Leu Gly Phe Arg Val Pro Cys Phe Val Ile Ser Pro Tyr Ser Arg Gly
385                 390                 395                 400

Gly Leu Met Val His Asp Arg Phe Asp His Thr Ser Gln Leu Gln Leu
                405                 410                 415

Ile Gly Lys Arg Phe Gly Val Pro Val Pro Asn Leu Thr Pro Trp Arg
                420                 425                 430

Ala Ser Val Thr Gly Asp Met Thr Ser Ala Phe Asn Phe Ala Ala Pro
            435                 440                 445

Pro Asp Pro Ser Pro Pro Asn Leu Asp His Pro Val Arg Gln Leu Pro
450                 455                 460

Lys Val Ala Lys Cys Val Pro Asn Val Val Leu Gly Phe Leu Asn Glu
465                 470                 475                 480

Gly Leu Pro Tyr Arg Val Pro Tyr Pro Gln Thr Thr Pro Val Gln Glu
                485                 490                 495

Ser Gly Pro Ala Arg Pro Ile Pro Ser Gly Ile Cys
                500                 505

<210> SEQ ID NO 8
<211> LENGTH: 280
<212> TYPE: PRT
<213> ORGANISM: Mycobacterium tuberculosis

<400> SEQUENCE: 8

Asp Ala Gly Val Ser Trp Lys Val Tyr Arg Asn Lys Thr Leu Gly Pro
1               5                   10                  15

Ile Ser Ser Val Leu Thr Tyr Gly Ser Leu Val Thr Ser Phe Lys Gln
                20                  25                  30

Ser Ala Asp Pro Arg Ser Asp Leu Val Arg Phe Gly Val Ala Pro Ser
            35                  40                  45

Tyr Pro Ala Ser Phe Ala Ala Asp Val Leu Ala Asn Arg Leu Pro Arg
50                  55                  60

Val Ser Trp Val Ile Pro Asn Val Leu Glu Ser His Pro Ala Val
65                  70                  75                  80

Pro Ala Ala Ala Gly Ala Phe Ala Ile Val Asn Ile Leu Arg Ile Leu
                85                  90                  95

Leu Ala Asn Pro Ala Val Trp Glu Lys Thr Ala Leu Ile Val Ser Tyr
                100                 105                 110

Asp Glu Asn Gly Gly Phe Phe Asp His Val Val Pro Thr Ala Pro
            115                 120                 125

Ala Gly Thr Pro Gly Glu Tyr Val Thr Val Pro Asp Ile Asp Gln Val
            130                 135                 140

Pro Gly Ser Gly Gly Ile Arg Gly Pro Ile Gly Leu Gly Phe Arg Val
145                 150                 155                 160
```

```
Pro Cys Phe Val Ile Ser Pro Tyr Ser Arg Gly Pro Gln Met Val His
                165                 170                 175

Asp Thr Phe Asp His Thr Ser Gln Leu Arg Leu Leu Glu Thr Arg Phe
            180                 185                 190

Gly Val Pro Val Pro Asn Leu Thr Ala Trp Arg Arg Ser Val Thr Gly
        195                 200                 205

Asp Met Thr Ser Thr Phe Asn Phe Ala Val Pro Pro Asn Ser Ser Trp
    210                 215                 220

Pro Asn Leu Asp Tyr Pro Gly Leu His Ala Leu Ser Thr Val Pro Gln
225                 230                 235                 240

Cys Val Pro Asn Ala Ala Leu Gly Thr Ile Asn Arg Gly Ile Pro Tyr
                245                 250                 255

Arg Val Pro Asp Pro Gln Ile Met Pro Thr Gln Glu Thr Thr Pro Thr
            260                 265                 270

Arg Gly Ile Pro Ser Gly Pro Cys
        275                 280

<210> SEQ ID NO 9
<211> LENGTH: 514
<212> TYPE: PRT
<213> ORGANISM: Mycobacterium tuberculosis

<400> SEQUENCE: 9

Met Ser Gln Ser His Ile Gly Gly Val Ser Arg Arg Glu Phe Leu Ala
1               5                   10                  15

Lys Val Ala Ala Gly Ala Gly Ala Leu Met Ser Phe Ala Gly Pro
                20                  25                  30

Val Ile Glu Lys Ala Tyr Gly Ala Gly Pro Cys Ser Gly His Leu Thr
                35                  40                  45

Asp Ile Glu His Phe Val Phe Met Gln Glu Asn Arg Ser Phe Asp
    50                  55                  60

His Tyr Phe Gly Thr Leu Ser Gly Thr Asp Gly Phe Asn Thr Val Ser
65                  70                  75                  80

Pro Leu Phe Gln Gln Lys Gly Trp Asn Pro Met Thr Gln Ala Leu Asp
                85                  90                  95

Ala Thr Gly Val Thr Met Pro Tyr Arg Phe Asp Thr Thr Arg Gly Pro
                100                 105                 110

Phe Leu Asp Gly Ala Cys Val Asn Asp Pro Asp His Ser Trp Val Ala
            115                 120                 125

Met His Glu Ser Trp Asn Gly Gly Val Asn Asp Asn Trp Leu Pro Ala
    130                 135                 140

Gln Ala Lys Thr Arg Ser Ala Ala His Thr Pro Thr Val Met Gly Tyr
145                 150                 155                 160

Tyr Thr Arg Gln Asp Ile Pro Ile His Tyr Leu Leu Ala Asp Ala Phe
                165                 170                 175

Thr Val Cys Asp Arg Tyr Phe Cys Ser Val Leu Gly Pro Thr Leu Pro
            180                 185                 190

Asn Arg Leu Tyr Trp Leu Ser Ala Thr Ile Asp Pro Asp Gly Gln Asn
        195                 200                 205

Gly Gly Pro Glu Leu Gln Ser Pro Thr Phe Gln Pro Val Arg Arg Phe
    210                 215                 220

Gly Trp Arg Ile Met Pro Gln Asn Leu Ser Asp Ala Gly Val Ser Trp
225                 230                 235                 240

Lys Val Tyr Arg Asn Lys Thr Leu Gly Pro Ile Ser Ser Val Leu Thr
                245                 250                 255
```

```
Tyr Gly Ser Leu Val Thr Ser Phe Lys Gln Ser Ala Asp Pro Arg Ser
            260                 265                 270

Asp Leu Val Arg Phe Gly Val Ala Pro Ser Tyr Pro Ala Ser Phe Ala
        275                 280                 285

Ala Asp Val Leu Ala Asn Arg Leu Pro Arg Val Ser Trp Val Ile Pro
    290                 295                 300

Asn Val Leu Glu Ser Glu His Pro Ala Val Pro Ala Ala Ala Gly Ala
305                 310                 315                 320

Phe Ala Ile Val Asn Ile Leu Arg Ile Leu Leu Ala Asn Pro Ala Val
                325                 330                 335

Trp Glu Lys Thr Ala Leu Ile Val Ser Tyr Asp Glu Asn Gly Gly Phe
            340                 345                 350

Phe Asp His Val Val Pro Ala Thr Ala Pro Ala Gly Thr Pro Gly Glu
        355                 360                 365

Tyr Val Thr Val Pro Asp Ile Asp Gln Val Pro Gly Ser Gly Gly Ile
    370                 375                 380

Arg Gly Pro Ile Gly Leu Gly Phe Arg Val Pro Cys Phe Val Ile Ser
385                 390                 395                 400

Pro Tyr Ser Arg Gly Pro Gln Met Val His Asp Thr Phe Asp His Thr
                405                 410                 415

Ser Gln Leu Arg Leu Leu Glu Thr Arg Phe Gly Val Pro Val Pro Asn
            420                 425                 430

Leu Thr Ala Trp Arg Arg Ser Val Thr Gly Asp Met Thr Ser Thr Phe
        435                 440                 445

Asn Phe Ala Val Pro Pro Asn Ser Ser Trp Pro Asn Leu Asp Tyr Pro
    450                 455                 460

Gly Leu His Ala Leu Ser Thr Val Pro Gln Cys Val Pro Asn Ala Ala
465                 470                 475                 480

Leu Gly Thr Ile Asn Arg Gly Ile Pro Tyr Arg Val Pro Asp Pro Gln
                485                 490                 495

Ile Met Pro Thr Gln Glu Thr Thr Pro Thr Arg Gly Ile Pro Ser Gly
            500                 505                 510

Pro Cys

<210> SEQ ID NO 10
<211> LENGTH: 336
<212> TYPE: PRT
<213> ORGANISM: Mycobacterium tuberculosis

<400> SEQUENCE: 10

Met Ala Lys Asn Ser Arg Arg Lys Arg His Arg Ile Leu Ala Trp Ile
1               5                   10                  15

Ala Ala Gly Ala Met Ala Ser Val Val Ala Leu Val Ile Val Ala Val
            20                  25                  30

Val Ile Met Leu Arg Gly Ala Glu Ser Pro Pro Ser Ala Val Pro Pro
        35                  40                  45

Gly Val Leu Pro Pro Gly Pro Thr Pro Ala His Pro His Lys Pro Arg
    50                  55                  60

Pro Ala Phe Gln Asp Ala Ser Cys Pro Asp Val Gln Met Ile Ser Val
65                  70                  75                  80

Pro Gly Thr Trp Glu Ser Ser Pro Gln Gln Asn Pro Leu Asn Pro Val
                85                  90                  95

Gln Phe Pro Lys Ala Leu Leu Leu Lys Val Thr Gly Pro Ile Ala Gln
            100                 105                 110
```

-continued

```
Gln Phe Ala Pro Ala Arg Val Gln Thr Tyr Thr Val Ala Tyr Thr Ala
            115                 120                 125
Gln Phe His Asn Pro Leu Thr Thr Asp Asn Gln Met Ser Tyr Asn Asp
            130                 135                 140
Ser Arg Ala Glu Gly Thr Arg Ala Met Val Ala Ala Met Thr Asp Met
145                 150                 155                 160
Asn Asn Arg Cys Pro Leu Thr Ser Tyr Val Leu Ile Gly Phe Ser Gln
                165                 170                 175
Gly Ala Val Ile Ala Gly Asp Val Ala Ser Asp Ile Gly Asn Gly Arg
                180                 185                 190
Gly Pro Val Asp Glu Asp Leu Val Leu Gly Val Thr Leu Ile Ala Asp
                195                 200                 205
Gly Arg Arg Gln Gln Gly Val Gly Asn Gln Val Pro Pro Ser Pro Arg
            210                 215                 220
Gly Glu Gly Ala Glu Ile Thr Leu His Glu Val Pro Val Leu Ser Gly
225                 230                 235                 240
Leu Gly Leu Thr Met Thr Gly Pro Arg Pro Gly Gly Phe Gly Ala Leu
                245                 250                 255
Asp Gly Arg Thr Asn Glu Ile Cys Ala Gln Gly Asp Leu Ile Cys Ala
                260                 265                 270
Ala Pro Ala Gln Ala Phe Ser Pro Ala Asn Leu Pro Thr Thr Leu Asn
            275                 280                 285
Thr Leu Ala Gly Gly Ala Gly Gln Pro Val His Ala Met Tyr Ala Thr
            290                 295                 300
Pro Glu Phe Trp Asn Ser Asp Gly Glu Pro Ala Thr Glu Trp Thr Leu
305                 310                 315                 320
Asn Trp Ala His Gln Leu Ile Glu Asn Ala Pro His Pro Lys His Arg
                325                 330                 335
```